United States Patent [19]

Milner

[11] Patent Number: 4,555,363
[45] Date of Patent: Nov. 26, 1985

[54] PROCESS FOR THE PREPARATION OF β-LACTAM COMPOUNDS

[75] Inventor: Peter H. Milner, Rudgwick, England

[73] Assignee: Beecham Group p.l.c., England

[21] Appl. No.: 572,196

[22] Filed: Jan. 19, 1984

[30] Foreign Application Priority Data

Jan. 21, 1983 [GB] United Kingdom ............... 8301688
Jun. 24, 1983 [GB] United Kingdom ............... 8317199

[51] Int. Cl.$^4$ ............... C07D 499/04; C07D 501/02
[52] U.S. Cl. ............... 260/239.1; 260/245.2 R; 544/21
[58] Field of Search ............... 260/239.1, 245.2 R; 544/21; 564/218, 222

[56] References Cited

U.S. PATENT DOCUMENTS 2,647,815  8/1953  Buc et al. ............... 564/218

OTHER PUBLICATIONS

The Journal of Organic Chemistry, vol. 38, No. 7, 6th-Apr. 1973 pp. 1436-1437.

Tetrahedron Letters, No. 34, 1975, pp. 2955-2958, Pergamon Press, GB.

*Primary Examiner*—Natalie Trousof
*Assistant Examiner*—Vera C. Clarke
*Attorney, Agent, or Firm*—Jacobs & Jacobs

[57] ABSTRACT

A process for the preparation of a β-lactam having the partial structure (I):

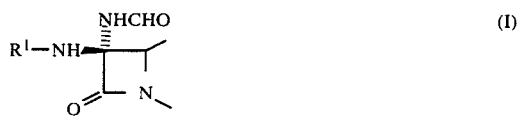

wherein $R_1$ is an acyl group, which process comprises treating an imine having the partial structure (II):

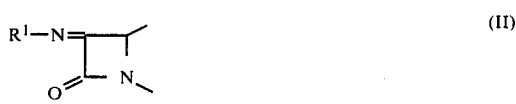

with a nucleophilic derivative of formamide.

9 Claims, No Drawings

PROCESS FOR THE PREPARATION OF β-LACTAM COMPOUNDS

This invention relates to a chemical process for the preparation of β-lactam compounds, and in particular for the introduction of a formamido substituent into a β-lactam having an acylamino side chain. Certain of the substituted β-lactam compounds produced by this process are antibacterial agents; others are useful as intermediates for producing such agents. Each of these groups is described below.

The present invention provides a process for the preparation of a β-lactam having the partial structure (I):

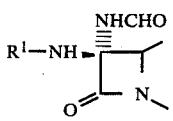    (I)

wherein $R^1$ is an acyl group, which process comprises treating an imine having the partial structure (II)

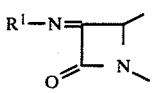    (II)

with a nucleophilic derivative of formamide.

Suitably the acyl group for $R^1$ is a carboxylic acyl group. Other suitable acyl groups for $R^1$ include sulphonyl and phosphonyl groups.

Suitable nucleophilic derivatives of formamide include N-silyl, N-stannyl and N-phosphorylated derivatives.

By the term 'N-silyl derivative' of formamide we mean the product of reaction of the amino group of formamide with a silylating agent such as a halosilane or a silazane of the formula:

$L_3Si.U$; $L_2Si.U_2$; $L_3Si.NL_2$;
$L_3Si.NH.SiL_3$; $L_3Si.NH.COL$; $L_3Si.NH.CO.NH.SiL_3$;
$LNH.CO.NH.SiL_3$;

wherein U is a halogen and the various groups L which may be the same or different, each represents hydrogen or alkyl, alkoxy, aryl, or aralkyl. Preferred silylating agents are silyl chlorides, particularly trimethylchlorosilane.

The term 'N-stannyl derivative' of formamide includes the product of reaction of the amino group of formamide with a stannylating agent such as a halostannane of formula:

    $L_3SnU$ wherein L and U are as defined hereinbefore.

The term 'N-phosphorylated' derivative of formamide is intended to include compounds wherein the amino group of formamide is substituted with a group of formula:

    $-P.R_aR_b$ wherein $R_a$ is an alkyl, haloalkyl, aryl, aralkyl, alkoxy, haloalkoxy, aryloxy, aralkyloxy or dialkylamino group, $R_b$ is the same as $R_a$ or is halogen or $R_a$ and $R_b$ together form a ring.

Other suitable nucleophilic derivatives of formamide include

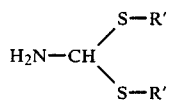

wherein R' and R" may be the same or different and each represent a $C_{1-6}$ alkyl group or R' and R" together represent a $C_{2-4}$ alkylene di-radical.

Preferably the nucleophilic derivative of formamide is a N,N-bis(tri-loweralkylsilyl)formamide, in particular N,N-bis(trimethylsilyl)formamide.

Suitable solvents in which the reaction may be performed include for example, dioxan, tetrahydrofuran, dimethylformamide, and hexamethylphosphoramide. The reactions are generally carried out under an inert atmosphere and at moderate to low temperatures ie in the range $-100°$ C. to $+30°$ C. The course of the reaction may be followed by conventional methods such as thin layer chromatography and terminated when an optimum quantity of product is present in the reaction mixture.

Subsequent to the reaction it may be necessary to regenerate the formamido group from any derivative; suitable methods include those known in the art such as, for example, acid or base hydrolysis or treatment with a metal ion such as mercury, silver, thallium, lead or copper.

In a further aspect the present invention provides a process for the preparation of a compound of formula (III) or a salt thereof:

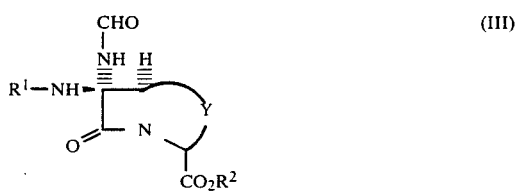    (III)

wherein $R^1$ is as defined hereinbefore; $R^2$ is hydrogen or a readily removable carboxyl protecting group; and Y is:

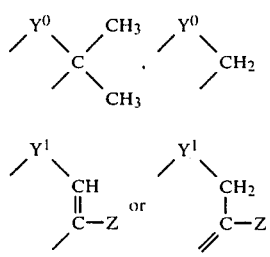

wherein $Y^0$ is sulphur, SO or $SO_2$, $Y^1$ is oxygen, sulphur, SO, $SO_2$ or $-CH_2-$ and Z represents hydrogen, halogen, or an organic group such as $C_{1-4}$ alkoxy, $-CH_2Q$ or $-CH=CH-Q$ wherein Q represents hydrogen, halogen, hydroxy, mercapto, cyano, carboxy, carbamoyloxy, carboxylic ester, $C_{1-4}$ alkyloxy, acyloxy, aryl, a heterocyclyl group bonded via carbon, a heterocyclylthio group or a nitrogen containing heterocyclic group bonded via nitrogen, which process comprises treating an intermediate imine of formula (IV):

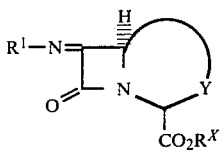 (IV)

wherein any reactive groups may be protected; $R^1$ and Y are as hereinbefore defined and wherein any reactive groups may be protected; and $R^x$ is a readily removable carboxy protecting group; with a nucleophilic derivative of formamide and thereafter, if necessary, carrying out one or more of the following steps:
 (i) removing any protecting groups;
 (ii) converting a group $R^x$ to a group $R^2$;
 (iii) converting one group Z into a different group Z;
 (iv) converting the product into a salt.

When used herein the term 'halogen' unless otherwise defined is suitably fluorine, chlorine, bromine and iodide, preferably chlorine and bromine.

When used herein the term 'carboxylic ester' unless otherwise defined suitably include $C_{1-6}$ alkyl esters.

When used herein the term 'acyloxy' unless otherwise defined suitably includes $C_{1-6}$ alkylcarbonyloxy groups.

When used herein the term 'aryl' unless otherwise defined suitably includes phenyl and naphthyl, preferably phenyl, optionally substituted with up to five halogen, $C_{1-6}$ alkyl, $C_{1-6}$ alkoxy, halo($C_{1-6}$) alkyl, hydroxy, amino, carboxy, $C_{1-6}$ alkoxycarbonyl, or $C_{1-6}$ alkoxycarbonyl-($C_{1-6}$)-alkyl groups.

When used herein the term 'heterocyclyl' unless otherwise defined suitably includes single or fused rings comprising up to four hetero atoms in the ring selected from oxygen, nitrogen, and sulphur and optionally substituted with up to three halogen, $C_{1-6}$ alkyl, $C_{1-6}$ alkoxy, halo-($C_{1-6}$)-alkyl, hydroxy, amino, carboxy, $C_{1-6}$ alkoxycarbonyl, $C_{1-6}$ alkoxycarbonyl($C_{1-6}$) alkyl, aryl, oxo, carboxy($C_{1-6}$)alkyl, carbamoyl-($C_{1-6}$)alkyl, amino($C_{1-6}$)alkyl, substituted amino($C_{1-6}$) alkyl or sulphonyl($C_{1-6}$)alkyl groups.

When used herein the term 'lower' indicates that the group contains 1 to 6 carbon atoms.

Suitably Y is:

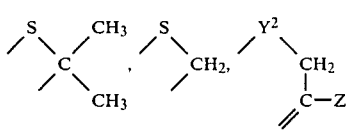

wherein $Y^2$ is oxygen, sulphur or —$CH_2$— and Z is as hereinbefore defined.

Preferred values for Y in the compounds of formula (III) are —S—C($CH_3$)$_2$— and —S—$CH_2$—C($CH_2$Q)=, ie when the compound of formula (III) is a derivative of a penicillin or cephalosporin.

A particularly preferred value for Y is —S—C($CH_3$)$_2$—.

A further preferred value for Y is —S—$CH_2$—CZ= wherein Z is as hereinbefore defined.

The acyl group for $R^1$ is suitably an acyl group of an antibacterially active penicillin or cephalosporin. Suitable groups $R^1$ include those of formula $R^3CO$— as defined below.

The acyl group for $R^1$ is also suitably a removable amino-protecting acyl group.

Examples of removable amino-protecting acyl groups for $R^1$ include benzyloxycarbonyl optionally substituted in the phenyl ring by one or two substituents selected from $C_{1-4}$ alkyl, $C_{1-4}$ alkoxy, trifluoromethyl, halogen or nitro; $C_{1-4}$ alkoxycarbonyl, for example tert-butoxycarbonyl; allyloxycarbonyl; or trichloroethoxycarbonyl.

Suitable removable amino-protecting acyl groups $R^1$ are those well-known in the art which may be removed under conventional conditions without disruption of the remainder of the molecule.

Preferred examples of removable amino-protecting acyl groups within $R^1$ include those listed above which are removable under acid conditions optionally in the presence of a group IIb metal.

It will be appreciated that removal of an amino protecting acyl group $R^1$ gives the β-amino derivative of the β-lactam.

Those compounds of the formula (III) wherein $R^2$ is a readily removable carboxyl protecting group or a non-pharmaceutically acceptable salt, are primarily useful as intermediates in the preparation of compounds of the formula (III) wherein $R^2$ is a free carboxyl group or a pharmaceutically acceptable salt thereof. The conversion referred to above may be accomplished by procedures per se well known in the art. Also included within the readily removable carboxyl protecting groups $R^2$ are pharmaceutically acceptable in vivo hydrolysable ester groups.

The antibacterial compounds produced by the process of the present invention are formulated into pharmaceutical compositions according to techniques per se known in the art and are administered by conventional routes and dosage rates; for example, as disclosed in U.S. patent application Ser. No. 401,266 and European Patent Application No. 8230382.1 (publication No. 0071395) which are incorporated herein by reference.

Examples of suitable pharmaceutically acceptable in vivo hydrolysable ester groups include those which break down readily in the human body to leave the parent acid or its salt. Suitable ester groups of this type include those of part formula (i), (ii) and (iii):

 (i)

 (ii)

 (iii)

wherein $R^a$ is hydrogen, methyl, or phenyl, $R^b$ is $C_{1-6}$ alkyl, $C_{1-6}$ alkoxy or phenyl; or $R^a$ and $R^b$ together form a 1,2-phenylene group optionally substituted by one or two methoxy groups; $R^c$ represents $C_{1-6}$ alkylene optionally substituted with a methyl or ethyl group—$R^d$ and $R^e$ independently represent $C_{1-6}$ alkyl; $R^f$ represents $C_{1-6}$ alkyl.

Examples of suitable in vivo hydrolysable ester groups include for example acyloxyalkyl groups such as acetoxymethyl, pivaloyloxymethyl, α-acetoxyethyl and α-pivaloyloxyethyl groups; alkoxycarbonyloxyalkyl groups such as ethoxycarbonyloxymethyl and α-ethoxycarbonyloxyethyl; dialkylaminoalkyl especially di-loweralkylamino alkyl groups; such as dimethylaminomethyl, dimethylaminoethyl, diethylaminomethyl or diethylaminoethyl; lactone groups such as phthalidyl and dimethoxyphthalidyl; and esters linked to a second β-lactam antibiotic or to a β-lactamase inhibitor.

Suitable readily removable carboxyl protecting groups for the group —CO$_2$R$^2$ in formula (III) and —CO$_2$R$^x$ in formula (IV) include salt and ester derivatives of the carboxylic acid. The derivative is preferably one which may readily be cleaved.

Suitable ester-forming carboxyl-protecting groups are those which may be removed under conventional conditions. Such groups for R$^2$ and R$^x$ include benzyl, p-methoxybenzyl, benzoylmethyl, p-nitrobenzyl, 4-pyridylmethyl, 2,2,2-trichloroethyl, 2,2,2-tribromoethyl, t-butyl, t-amyl, allyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, acetonyl, p-toluenesulphonylethyl, methoxymethyl, a silyl, stannyl or phosphorus-containing group, an oxime radical of formula —N=CHR$^o$ where R$^o$ is aryl or heterocyclic, or an in vivo hydrolysable ester radical such as defined above.

The carboxyl group may be regenerated from any of the above esters by usual methods appropriate to the particular R$^2$ or R$^x$ group, for example, acid—and base—catalysed hydrolysis, or by enzymically-catalysed hydrolysis, or by hydrogenolysis.

Suitable pharmaceutically acceptable salts of the carboxy group of the compound of formula (III) include metal salts eg aluminium, alkali metal salts such as sodium or potassium, alkaline earth metals salts such as calcium or magnesium and ammonium or substituted ammonium salts, for example those with lower alkylamines such as triethylamine, hydroxy-lower alkylamines such as 2-hydroxyethylamine, bis-(2-hydroxyethyl)-amine or tris-(2-hydroxyethyl)-amine, cycloalkylamines such as dicyclohexylamine, or with procaine, dibenzylamine, N,N-dibenzylethylene-diamine, 1-ephenamine, N-ethylpiperidine, N-benzyl-β-phenethylamine, dehydroabietylamine, N,N'-bisdehydroabietylamine, ethylenediamine, or bases of the pyridine type such as pyridine, collidine or quinoline, or other amines which have been used to form salts with known penicillins and cephalosporins. Other suitable salts include the lithium and silver salt.

Suitable values for Q in the compounds of the formula (III) include the acetoxy, heterocyclylthio group, and nitrogen containing heterocyclic group bonded via nitrogen.

More suitably Q represents the acetoxy or heterocyclylthio group.

The heterocyclylthio group may suitably be represented by the formula:

—S—Het wherein 'Het' is a five or six membered heterocyclic ring containing from 1 to 4 atoms selected from N, O, and S unsubstituted or substituted with one or two groups selected from C$_{1-6}$ alkyl, C$_{1-6}$ alkoxy, hydroxyalkyl, C$_{1-6}$ alkenyl, alkoxyalkyl, carboxyalkyl, sulphonylalkyl, carbamoylalkyl, trifluoromethyl, hydroxy, halogen, oxo, optionally substituted aminoalkyl, and carboxy-alkyl or two substituents may be linked to form the residue of a heterocyclic or carbocyclic ring.

Examples of the group 'Het' include unsubstituted and substituted imidazolyl, triazolyl, tetrazolyl, thiazolyl, thiadiazolyl, thiatriazolyl, oxazolyl, triazinyl and oxadiazolyl.

Suitable groups 'Het' include unsubstituted and substituted 1,2,3-triazolyl; 1,2,4-triazolyl; tetrazolyl; oxazolyl; thiazolyl; 1,3,4-oxadiazolyl; 1,3,4-thiadiazolyl; or 1,2,4-thiadiazolyl. Preferably the heterocyclylthio group is 1-methyl-1H-tetrazol-5-ylthio, 2-methyl-1,3,4-thiadiazol-5-ylthio, 1-carboxymethyl-1H-tetrazol-5-ylthio or 6-hydroxy-2-methyl-5-oxo-2H-1,2,4-triazin-3-ylthio.

The nitrogen containing heterocyclic group bonded via nitrogen is suitably a pyridinium group unsubstituted or substituted with one or two groups selected from C$_{1-6}$ alkyl, C$_{1-6}$ alkoxy, hydroxyalkyl, C$_{1-6}$ alkenyl, alkoxyalkyl, carboxyalkyl, sulphonylalkyl, carbamoylmethyl, carbamoyl, trifluoromethyl, hydroxy, halogen, oxo, aminoalkyl, or two substituents on adjacent carbon atoms may form the residue of a carbocyclic ring.

Preferred compounds produced by the process of this invention can be represented by the formula (V) or a pharmaceutically acceptable salt or in vivo hydrolysable ester thereof:

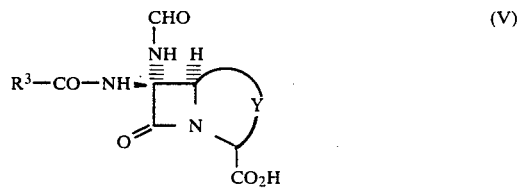

wherein Y is as defined with respect to formula (III); and R$_3$ is a group such that R$_3$—CO—NH— is an acylamino group in particular that as found in antibacterially active penicillins or cephalosporins.

Suitable groups R$_3$CO— for inclusion in the compounds of the formula (V) include those of the sub-formulae (a)—(e):

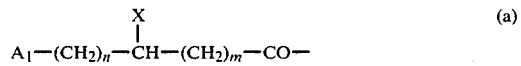 (a)

 (b)

 (c)

 (d)

 (e)

wherein n is 0, 1 or 2; m is 0, 1 or 2; A$_1$ is C$_{1-6}$ alkyl, substituted C$_{1-6}$ alkyl, C$_{3-6}$ cycloalkyl, cyclohexenyl, cyclohexadienyl, an aromatic group, such as phenyl, substituted phenyl, thienyl, pyridyl, an optionally substituted thiazolyl group a C$_{1-6}$ alkylthio group or C$_{1-6}$ alkyloxy; X is a hydrogen or halogen atom, a carboxylic acid, carboxylic ester, sulphonic acid, azido, tetrazolyl, hydroxy, acyloxy, amino, ureido, acylamino, heterocyclylamino, guanidino or acylureido group; $A_2$ is an aromatic group such as a phenyl, a 2,6-dimethoxyphenyl, 2-alkoxy-1-naphthyl, 3-arylisoxazolyl, 3-aryl-5-methylisoxazolyl group a substituted alkyl group, or a substituted dithietane; $X_1$ is a $CH_2OCH_2$, $CH_2SCH_2$ or $(CH_2)_n$ group; $X_2$ is an oxygen or suphur atom; $A_3$ is an aryl or heteroaryl group such as phenyl, substituted phenyl or aminothiazolyl; and $A_4$ is hydrogen, $C_{1-6}$ alkyl, $C_{3-6}$ cycloalkyl, arylaminocarbonyl, $C_{1-6}$ alkylaminocarbonyl, $C_{1-6}$ alkanoyl, $C_{1-6}$ alkoxycarbonyl, $C_{2-6}$ alkenyl, carboxy $C_{1-6}$ alkyl, $C_{1-6}$ alkylsulphonyl and di-$C_{1-6}$ alkylphosphatomethyl.

More suitably $A_1$ is $C_{1-6}$ alkyl, $C_{3-6}$ cycloalkyl, cyclohexenyl, cyclohexadienyl, phenyl, hydroxyphenyl, thienyl or pyridyl group; and X is a hydrogen or halogen atom, a carboxylic acid, carboxylic ester, azido, tetrazolyl, hydroxy, acyloxy, amino, ureido, guanidino or acylureido group.

Other more suitable groups $A_1$ include dihydroxyphenyl, di($C_{1-6}$)alkanoyloxyphenyl such as diacetoxyphenyl and di($C_{1-6}$)alkoxycarbonylphenyl, such as diethoxycaronyloxyphenyl.

Favoured groups $R^3$ for inclusion in the compounds of the formula (V) include those of the sub-formula (f) and (g):

 (f)

 (g)

wherein $R^4$ is a phenyl, thienyl or phenoxy group; $R^5$ is a hydrogen atom or methyl group; $R^6$ is a phenyl, substituted phenyl, substituted thiazolyl, thienyl or cyclohexadienyl group; and $R^7$ is a hydroxyl, carboxylic acid group or lower alkyl or phenyl, tolyl or indanyl ester thereof, amino or a substituted amino group.

Suitably the substituted phenyl group for $R^6$ is a phenyl group substituted with up to three groups selected from $C_{1-6}$ alkyl, phenyl, halogen, $C_{1-6}$ alkoxy, amino, nitro, hydroxy, $C_{1-6}$ alkylamido, $C_{1-6}$ alkylcarbonyloxy, carboxy, $C_{1-6}$ alkoxycarbonyl, $C_{1-6}$ alkoxycarbonyloxy, halo($C_{1-6}$)alkyl, oxo($C_{1-6}$)alkyl, $C_{1-6}$ alkylcarbonyl, aryloxy, aralkyloxy, arylcarbonyl, $C_{1-6}$ alkylamino or di($C_{1-6}$)alkylamino.

Preferably $R^6$ is a phenyl, p-hydroxyphenyl, thienyl or cyclohexadienyl group.

Other preferred groups $R^6$ include 3,4-dihydroxyphenyl and 3,4-diacetoxyphenyl.

Preferably $R^7$ is a substituted amino group.

More preferably the substituted amino group $R^7$ is a ureido, acylamino or acylureido group.

One suitable sub-group of compounds produced by the process of the present invention provides a compound of formula (VI) or a pharmaceutically acceptable salt or in vivo hydrolysable ester thereof:

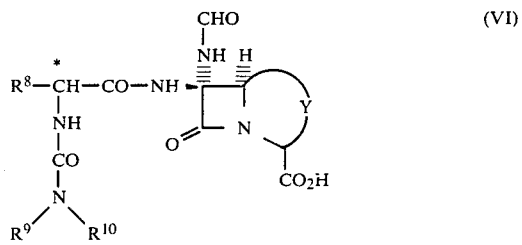 (VI)

wherein Y is as defined with respect to formula (III) and $R^8$ is phenyl, substituted phenyl, cyclohexenyl, cyclohexadienyl, or a 5- or 6-membered heterocyclic ring containing up to three hetero-atoms selected from oxygen, sulphur or nitrogen, optionally substituted with hydroxy, amino, halogen, substituted amino or $C_{1-6}$ alkoxy; $R^9$ is hydrogen, a $C_{1-6}$ alkyl group or substituted $C_{1-6}$ alkyl group and $R^{10}$ is an optionally substituted 5- or 6-membered heterocyclic group containing one or two nitrogen heteroatoms; or $R^9$ and $R^{10}$ together with the nitrogen atom to which they are attached form an optionally substituted five- or six-membered heterocyclic group containing one or two nitrogen heteroatoms.

Suitably the substituted phenyl group for $R^8$ is a phenyl group substituted with up to three groups selected from $C_{1-6}$ alkyl, phenyl, halogen, $C_{1-6}$ alkoxy, amino, nitro, hydroxy, $C_{1-6}$ alkylamido, $C_{1-6}$ alkylcarbonyloxy, carboxy, $C_{1-6}$ alkoxycarbonyl, halo ($C_{1-6}$)alkyl, oxo($C_{1-6}$)alkyl, $C_{1-6}$ alkylcarbonyl, aryloxy, aralkyloxy, arylcarbonyl, $C_{1-6}$alkylamino or di($C_{1-6}$)alkylamino.

In formula (VI), the group $R^8$ is preferably phenyl, 4-hydroxyphenyl, 3,4-di($C_{1-6}$-alkylcarbonyloxy)-phenyl, 3,4-dihydroxyphenyl, 2-thienyl, 3-thienyl or 2-amino-4-thiazolyl.

Particularly preferred groups $R^8$ are 3,4-dihydroxyphenyl and 3,4-diacetoxyphenyl.

Suitably $R^9$ is hydrogen.

Suitable substituents for the 5- or 6-membered heterocyclic group of $R^{10}$ or $R^9$ and $R^{10}$ together include the optionally substituted alkyl, alkenyl, alkynyl, cycloalkyl or cycloalkenyl group; optionally substituted phenyl, oxo; the hydroxy group optionally substituted by alkyl, alkenyl, cycloalkyl, phenyl, pyridyl, pyrimidyl or benzyl; the optionally substituted mercapto group, the alkylsulphonyl group; the substituted imino group; or the amino group optionally substituted by an alkyl, alkenyl, cycloalkyl, phenyl, substituted phenyl or benzyl group. Alternatively two substituents on the ring may form the residue of a further carbocyclic or heterocyclic ring.

Preferred values for Y in the compounds of formulae (V) and (VI) are $—S—C(CH_3)_2—$ and $—S—CH_2C(CH_2Q)=$, wherein Q is hereinbefore defined ie when the compounds of formulae (V) and (VI) are derivatives of a penicillin or cephalosporin.

The carbon atom marked * in formulae herein is asymmetric so that the compounds may exist as two optically active diastereoisomers. In general that prepared from the D-side chain exhibits the highest antibacterial activity and accordingly the D compound or the DL mixtures are preferred, with the D compound being particularly preferred.

Preferred compounds within formula (V) are the penicillin derivatives of formula (VII) or a pharmaceutically acceptable salt or in vivo hydrolysable ester thereof:

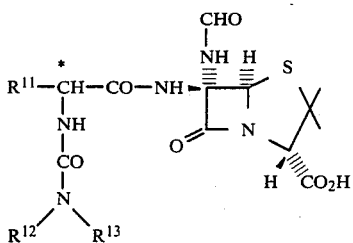

(VII)

wherein R¹¹ is phenyl, substituted phenyl, cyclohexenyl, cyclohexadienyl, or a 5- or 6-membered heterocyclic ring containing up to three heteroatoms selected from oxygen, sulphur or nitrogen, optionally substituted with hydroxy, amino, halogen or $C_{1-6}$ alkoxy, $R^{12}$ is hydrogen or $C_{1-6}$ alkyl and $R^{13}$ is an optionally substituted five- or six-membered heterocyclic group containing one or two nitrogen heteroatoms; or $R^{12}$ and $R^{13}$ together with the nitrogen atom to which they are attached form an optionally substituted five- or six-membered heterocyclic group containing one or two nitrogen heteroatoms.

In formula (VII) the group $R_{11}$ is preferably phenyl, 4-hydroxyphenyl, 2-thienyl, 3-thienyl, 2-amino-4-thiazolyl, 3,4-dihydroxyphenyl or 3,4-diacetoxyphenyl.

Particularly preferred groups $R^{11}$ include 3,4-dihydroxyphenyl and 3,4-diacetoxyphenyl.

Suitable substituents for the five- or six-membered heterocyclic group of $R^{13}$ or $R^{12}$ and $R^{13}$ together include the alkyl, alkenyl, alkynyl, cycloalkyl or cycloalkenyl group, optionally substituted phenyl, oxo, the hydroxy group optionally substituted by alkyl, alkenyl, cycloalkyl, phenyl, pyridyl, pyrimidyl or benzyl, the optionally substituted mercapto group, the alkylsulphonyl group, the substituted imino group, or the amino group optionally substituted by an alkyl, alkenyl, cycloalkyl, phenyl, substituted phenyl or benzyl group. Alternatively two substituents on the ring may form the residue of a further carbocyclic or heterocyclic ring.

Preferably $R^{12}$ is hydrogen.

One particularly preferred sub-group produced by the process of the present invention provides a compound of formula (VIII) or a pharmaceutically acceptable salt or in vivo hydrolysable ester thereof:

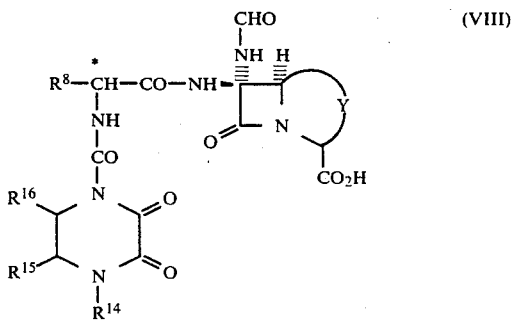

(VIII)

wherein $R^8$ and Y are as defined with respect to formula (VI) and $R^{14}$ represents hydrogen, $C_{1-6}$ alkyl, substituted alkyl, aryl, or aralkyl; $R^{15}$ and $R^{16}$ are the same or different and represent hydrogen, $C_{1-6}$ alkyl, substituted alkyl, halogen, amino, hydroxy or $C_{1-6}$ alkoxy or $R^{15}$ and $R^{16}$ form the residue of 5- or 6-membered carbocyclic or heterocyclic ring.

Suitable values for Y in the compounds of formula (VIII) are $-S-C(CH_3)_2-$ and $-S-CH_2-C(CH_2Q)=$ wherein Q is as hereinbefore defined.

Preferably Y in the compounds of formula (VIII) is $-S-C(CH_3)_2-$.

Preferred compounds within formula (VIII) are the penicillin derivatives of formula (IX) or a pharmaceutically acceptable salt or in vivo hydrolysable ester thereof:

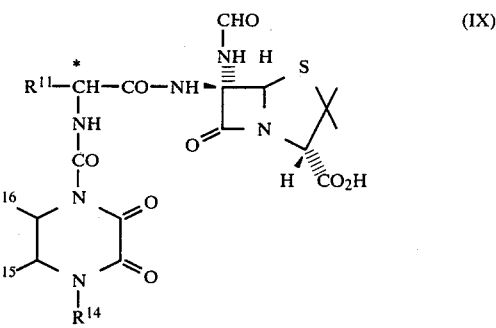

(IX)

wherein $R^{11}$, $R^{14}$, $R^{15}$ and $R^{16}$ are as hereinbefore defined.

Suitable $C_{1-6}$ alkyl groups for the groups $R^{14}$, $R^{15}$ and $R^{16}$ in formula (VIII) and formula (IX) include methyl, ethyl, n- and iso-propyl, n-, sec-, iso- and tert-butyl. Preferably $R^{14}$ is ethyl. Preferably $R^{15}$ and $R^{16}$ are hydrogen.

A further preferred subgroup of compounds produced by the process of the present invention are the compounds of formula (X) or a pharmaceutically acceptable salt or in vivo hydrolysable ester thereof:

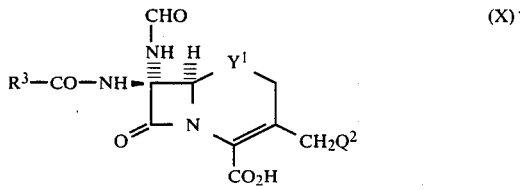

(X)

wherein $R^3$ and $Y^1$ are as hereinbefore defined; and $Q^2$ represents acetoxy; a group —SHet, wherein Het is as hereinbefore defined; or $Q^2$ represent a subgroup of formula (h):

(h)

wherein $R_q$ and $R_p$ may be the same or different and each represents hydrogen, $C_{1-6}$ alkyl, $C_{1-6}$ alkoxy, hydroxy-alkyl, $C_{1-6}$ alkenyl, alkoxyalkyl, carboxyalkyl, sulphonylalkyl, carbamoylalkyl, carbamoyl, trifluoromethyl, hydroxy, halogen, and aminoalkyl or $R_q$ and $R_p$ form the residue of a carbocyclic ring.

Suitable values of $R^3CO-$ within formula (X) are those of formulae (a) to (g) as hereinbefore defined with reference to formula (V).

Suitable groups 'Het' within formula (X) include substituted and unsubstituted 1,2,3-triazolyl; 1,2,4-triazolyl; tetrazolyl; oxazolyl; thiazolyl; 1,3,4-oxadiazolyl; 1,2,4-triazinyl; 1,3,4-thiadiazolyl or 1,2,4-thiadiazolyl. Preferably the groups 'S Het is 1-methyl-1$\overline{H}$-tetrazol-5-ylthio, 2-methyl-1,3,4-thiadiazol-5-ylthio, 1-carboxymethyl-1$\overline{H}$-tetrazol-5-ylthio or 6-hydroxy-2-methyl-5-oxo-2$\overline{H}$-1,2,4-triazin-3-ylthio.

Suitably $R_q$ represents hydrogen.

Suitably $R_p$ represents hydrogen, sulphonylalkyl or carbamoy, preferably the substituent $R_p$ is in the 4-position.

Suitably $Y^1$ is oxygen or sulphur.

More suitably $Y^1$ is oxygen.

More suitably $Y^1$ is sulphur.

Preferably $R^3$ within formula (X) is a subgroup of formula (j):

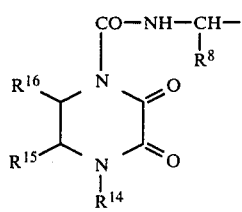

wherein $R^8$, $R^{14}$, $R^{15}$ and $R^{16}$ are as hereinbefore defined with reference to formula (VIII).

The imine of formula (IV) may suitably be prepared by treatment of a compound of formula (XI).

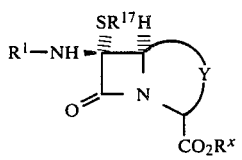

wherein $R^1$ and $R^x$ are as hereinbefore defined and wherein any reactive groups may be protected; and $R^{17}$ is $C_{1-6}$ alkyl, aryl, or benzyl with a metal ion such as mercury, silver, thallium, lead or copper.

Suitable examples of the alkyl group for $R^{17}$ include $C_{1-6}$ alkyl groups such as methyl, ethyl, n-, or iso-propyl, and n-, sec-, iso-, or tert-butyl groups.

A preferred alkyl group for $R^{17}$ is methyl.

Suitable examples of the aryl group $R^{17}$ include phenyl, optionally substituted with $C_{1-6}$ alkyl, $C_{1-6}$ alkoxy, halogen or nitro. Preferred aryl groups for $R^{17}$ include phenyl, o-, m- or p-methylphenyl, or o-, m- or p-nitrophenyl, in particular p-methylphenyl.

The preferred metal ion for use in the above process is the mercuric ion, aptly in the form of mercuric acetate.

Suitably such a reaction is performed at moderate to low temperature for example $-10°$ C. to $+30°$ C., and preferably ambient. The reaction is conveniently performed in an aprotic solvent such as tetrahydrofuran, dimethylformamide, hexamethylphosphoramide or dioxan.

The imine of formula (IV) may also suitably be prepared by treatment with base of a compound of formula (XII):

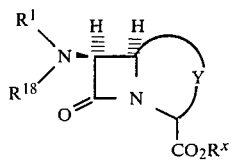

wherein $R^1$, $R^x$ and Y are as hereinbefore defined and wherein any reactive groups may be protected and $R^{18}$ is a leaving group.

Suitable leaving groups $R^{18}$ include trifluoromethanesulphonyl, pentafluorophenylsulphonyl, 4-nitrophenylsulphonyl, 2,4-dinitrophenylsulphonyl and nonafluorobentanesulphonyl.

More suitably $R^{18}$ is trifluoromethanesulphonyl.

Suitably the base for treatment of a compound of formula (XII) is non-nucleophilic. Preferably the base is a tri(lower alkyl)amine, such as for example triethylamine.

Suitable compounds within formula (XII) are those of formula (XIII):

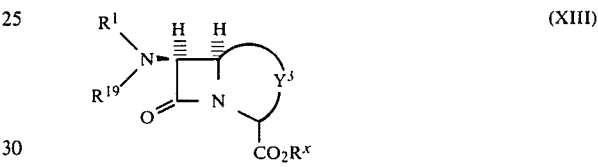

wherein $R^1$ and $R^x$ are as hereinbefore defined and wherein any reactive groups may be protected; Y3 is:

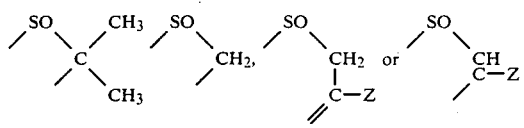

and $R^{19}$ is a leaving group.

Suitable leaving groups $R^{19}$ include those suitable under $R^{18}$.

Other suitable leaving groups $R^{19}$ include p-toluenesulphonyl and methanesulphonyl.

The imine of formula (IV) is also suitably prepared by processes per se known in the art such as, for example, those disclosed in European Patent Publication No. 0071395.

The imine of formula (IV) is often an unstable intermediate and is conveniently reacted with the nucleophilic derivative of formamide in situ without isolation of the imine (IV).

It will also be appreciated that the imine (II) may be generated in a similar manner to that described above from a compound of partial structure (XIV) or (XV):

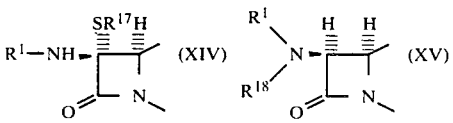

wherein $R^1$, $R^{17}$ and $R^{18}$ are as hereinbefore defined.

The compounds of formulae (XI) and (XIV) may suitably be prepared by processes such as, for example, those disclosed in copending U.S. patent application Ser. No. 401266 and European Patent Application No. 8230382.1 (Publication No. 0071395).

The compounds of formulae (XII), (XIII) and (XV) may be prepared by process as described or by processes analogous to those disclosed in European Patent Publication No. 0043546, D. Hagurara et al., J.C.S. Chem.Comm., 1982,578, and P.S.F. Mezes et al., Heterocycles, 1982,19, 1207.

The following Examples illustrate the process of the present invention.

EXAMPLE 1

Benzyl 6α-formamido-6β-(phenoxyacetamido)penicillanate

Mercuric acetate (0.160 g, 0.5 mmol) in dry N,N-dimethylformamide (1 ml) was added to a solution of benzyl $\neq\alpha$-(methylthio)-6β-(phenoxyacetamido)-penicillanate (0.243 g, 0.5 mmol) and N,N-bis(trimethylsily)formamide, (0.520 g, 2.75 mmol) under argon at room temperature. The reaction mixture was stirred at room temperature for 2 h before being poured into ethyl acetate (30 ml) and washed with water (6×30 ml), 0.1N hydrochloric acid (30 ml) and brine (30 ml). The organic solution was dried over magnesium sulphate, and then evaporated to afford the crude product. Chromatography on silica gel 60 (<230 mesh ASTM) eluting with hexane/ethyl acetate 1:1 afforded the title compound (0.160 g, 66%); $v_{max}$ (CH$_2$Cl$_2$) 3395, 3310, 1792, 1748, 1700, 1690 sh, 1495 cm$^{-1}$; δ (CDCl$_3$) 1.36 (6H,s, 2-CH$_3$'s), 4.51 (3H, s, PhOCH$_2$ and 3—H), 5.19 (2H,s, ester CH$_2$), 5.75 (1H, s, 5—H̄), 6.70–7.50 (10H, m, aromatics), 8.19 (1H, s, CHO), 8.23 (1H, s, 6β-amido proton) and 8.46 (1H, s, —NHCH̄O).

EXAMPLE 2

Benzyl 6α-formamido-6β-(phenoxyacetamido)penicillanate

Benzyl 6α-(methylthio)-6β-(phenoxyacetamido)-penicillanate (0.5 mmol) and N,N-bis(trimethylsily)-formamide (1 mmol) in N,N-dimethylformamide (5 ml) were treated with mercuric acetate (0.5 mmol) as described in Example 1. Chromatography afforded the title compound in 65% yield.

EXAMPLE 3

Benzyl 6α-formamido-6β-(phenoxyacetamido)penicillanate

Benzyl 6α-(methylthio)-6β-(phenoxyacetamido)-penicillanate (0.5 mmol) and N,N-bis(trimethylsilyl)formamide (1 mmol) in tetrahydrofuran (15 ml) were treated with mercuric acetate (0.5 mmol) as described in Example 1. Chromatography afforded the title compound in 64% yield.

EXAMPLE 4

Benzyl 6α-formamido-6β-(phenoxyacetamido)penicillanate

Cupric acetate monohydrate (0.100 g, 0.5 mmol) was added solid, in one portion, to a solution of benzyl 6α-(methylthio)-6β-(phenoxyacetamido)penicillanate (0.243 g, 0.5 mmol) and N,N-bis(trimethylsilyl)formamide (0.5 ml, 0.443 g, 2.34 mmol) in N,N-dimethylformamide (10 ml). The reaction mixture was stirred at room temperature for 2 h before being worked-up and chromatographed as described in Example 1. The title compound was obtained in 26% yield.

EXAMPLE 5

Benzyl 6β-[D-2-[(4-ethyl-2,3-dioxopiperazin-1-yl)carbonylamino]-2-(3,4-diacetoxyphenyl)acetamido]-6α-formamidopenicillanate Mercuric acetate (0.08 g, 0.25 mmol) in dry N,N-dimethylformamide (1 ml) was added to a solution of benzyl 6β-[D-2-[(4-ethyl-2,3-dioxopiperazin-1-yl)carbonylamino]-2-(3,4-diacetoxyphenyl)acetamido]-6α-(methylthio)-penicillanate (0.192 g, 0.25 mmol) and N,N-bis(trimethylsilyl)formamide (0.25 ml, 0.22 g, 1.17 mmol) in N,N-dimethylformamide (5 ml) at room temperature. The reaction mixture was stirred at room temperature under argon for 1 h before being poured into ethyl acetate (30 ml) and washed with water (6×30 ml) and brine (30 ml). After drying over magnesium sulphate, the organic solution was evaporated to afford the crude product, which was chromatographed on silica gel 60 (<230 mesh ASTM) eluting with 5% ethanol in ethyl acetate to give the title compound (0.075 g, 39%); $v_{max}$ (KBr) 1770, 1740, 1710, 1680 and 1500 cm$^{-1}$; δ(CDCl$_3$) 0.85 and 1.18 (6H, 2s, 2—CH$_3$'s), 1.23 (3H, t, J 7 Hz, CH$_3$CH$_2$N), 2.22 and 2.24 (6H, 2s, 2 CH$_3$CO), 3.40–3.60 (4H,m, 2CH$_2$N), 3.75–3.95 (2H,m, CH$_2$N), 4.36 (1H, s, 3—H), 5.12 (2H, s, PhCH$_2$O), 5.52 (1H, s, 5—H), 5.64 (1H, d, J 7 Hz, NCH̄CO), 7.12 (1H,d, J 7 Hz, aryl—H), 7.33 (6H, s, phenyl and one aryl-H), 7.45 (1H, d, J 7 Hz, aryl—H), 8.00–8.1 (2H, br s and sharp s, 1H on D$_2$O exch., NHCHO), 8.79 (1H, br s, D$_2$O exch, 6—NH) and 10.11 (1H, br d, J 7 Hz, NH̄CH).

EXAMPLE 6

(a) Benzyl 6β-[D-2-[(4-ethyl-2,3-dioxopiperazin-1-yl)carbonylamino]-2-(3,4-diacetoxyphenyl)acetamido]6α-formamidopenicillanate Benzyl 6β-[D-2-[(4-ethyl-2,3-dioxopiperazin-1-yl)carbonylamino]-2-(3,4-diacetoxyphenyl)acetamido]-6α-(methylthio)penicillanate (0.25 mmol) and N,N-bis(trimethylsilyl)formamide (0.5 mmol) in N,N-dimethylformamide (5 ml) were treated with mercuric acetate (0.25 mmol) as described in Example 5, to afford the title compound in 43% yield after chromatography.

(b) 6β-[D-2-[(4-Ethyl-2,3-dioxopiperazin-1-yl)carbonylamino]-2-(3,4-diacetoxyphenyl)]acetamido-6α-formamidopenicillanic acid, sodium salt Benzyl 6β-[D-2-[(4-Ethyl-2,3-dioxopiperazin-1-yl]-2-(3,4-diacetoxyphenyl)]acetamido-6α-formamidopenicillanate (0.100 g, 0.131 mmole) was dissolved in tetrahydrofuran:water (4:1, 10 ml), 10% palladium on charcoal (0.050 g) was added and the mixture was hydrogenated at ambient temperature and atmospheric pressure for 1 h. After this time no starting material was visible by t.l.c. The catalyst was filtered off and washed well with water and tetrahydrofuran. To the filtrate was added 2M sodium 2-ethylhexanoate in methyl isobutyl ketone (0.065 ml) and the solution was evaporated to dryness. Trituration of the residue with ether afforded an off-white solid which was filtered, well washed with acetone and ether, then dried to give the title penicillin sodium salt (0.060 g, 70%); $R_f$ 0.20 in n-butanol:acetic acid:water, 4:1:1, $v_{max}$(nujol) 1775, 1710 sh, 1680, 1610, 1500 cm$^{-1}$; δ(D$_2$O) 0.91 and 1.27 (6H, 2s, (CH$_3$)$_2$), 1.16

(3H, t, J 7 HZ, CH$_3$CH$_2$N), 2.30 (6H, s, 2 CH$_3$CO), 3.30–3.80 (4H, m, 2 CH$_2$N), 3.80–4.05 (2H, m, CH$_2$N), 4.15 (1H, s, 3—H), 5.46 (1H, s, 5—H, 5.56 (1H, s, NCHCO), 7.15–7.55 (3H, m, aryls), 8.07 (1H, s, NHCHO).

MIC (μg/ml) against P.mirabilis 889 is 0.5.

EXAMPLE 7

Benzyl 6β-[D-2-[(4-ethyl-2,3-dioxopiperazin-1-yl)carbonylamino]-2-(3,4-diacetoxyphenyl)acetamido]-6α-formamidopenicillanate Benzyl 6β-[D-2-[(4-ethyl-2,3-dioxopiperazin-1-yl)carbonylamino]-2-(3,4-diacetoxyphenyl)acetamido]-6α-(methylthio)penicillanate (0.25 mmol) and N,N-bis(-trimethylsilyl)formamide (0.5 mmol) in N,N-dimethylformamide (5 ml) at −20° C. were treated with mercuric acetate (0.5 mmol), and the reaction mixture was stirred at −20° C. under argon for 1 h. Work-up and chromatography as described in Example 5, afforded the title compound in 13% yield.

EXAMPLE 8

Benzyl 6β-[D-2-[(4-ethyl-2,3-dioxopiperazin-1-yl)carbonylamino]-2-(3,4-diacetoxyphenyl)acetamido]-6α-formamidopenicillanate Mercuric acetate (0.25 mmol) was added solid, in one portion to a solution of benzyl 6β-[D-2-[(4-ethyl-2,3-dioxopiperazin-1-yl)carbonylamino]-2-(3,4-diacetoxyphenyl)acetamido]-6α-(methylthio)penicillanate (0.25 mmol) and N,N-bis(trimethylsilyl)formamide (0.5 mmol) in dry tetrahydrofuran (10 ml) at room temperature. The reaction mixture was stirred under argon at room temperature for 2 h, before being worked-up and chromatographed as described in Example 5, to afford the title compound in 30% yield.

EXAMPLE 9

Benzyl 6β-[D-2-[(4-ethyl-2,3-dioxopiperazin-1-yl)carbonylamino]-2-(3,4-diacetoxyphenyl)acetamido]-6α-formamidopenicillanate Mercuric acetate (0.25 mmol) was added solid, in one portion, to a solution of benzyl 6β-[D-2-[(4-ethyl-2,3-dioxopiperazin-1-yl)carbonylamino]-2-(3,4-diacetoxyphenyl)acetamido]-6α-(methylthio)penicillanate (0.25 mmol) and N,N-bis(trimethylsilyl)formamide (0.5 mmol) in dry tetrahydrofuran (10 ml) at 0°–5° C. The reaction mixture was stirred at 0°–5° C. for 2 h, before being worked-up and chromatographed as in Example 5, to afford the title compound in 38% yield.

EXAMPLE 10

Benzyl 6αformamido-6β-(2,2,2-trichloroethoxycarbonylamino)penicillinate

Mercuric acetate (0.296 g, 0.93 mmol) in dry N,N-dimethylformamide (3 ml) was added dropwise to a solution of benzyl 6α-(methylthio)-6β-(2,2,2-trichloroethoxycarbonylamino)penicillanate (0.497 g, 0.93 mmol) and N,N-bis(trimethylsilyl)formamide (0.4 ml, 1.9 mmol) in N,N-dimethylformamide (10 ml) at room temperature. The reaction solution was stirred at room temperature under argon for 2 h. It was then poured into ethyl acetate (50 ml) and washed with water (5×30 ml), 1% aqueous sodium sulphide solution (3×30 ml), water (3×30 ml) and brine (30 ml). The organic solution was dried over magnesium sulphate, filtered and evaporated to afford the essentially pure product (0.438 g, 88%); ν$_{max}$ (KBr) 3340, 3160, 1790, 1745 and 1670 cm$^{-1}$; δ(CDCl$_3$) 1.37 and 1.53 (6H, 2s, 2—CH$_3$'s), 4.52 (1H, s, 3—H), 4.72 (2H, s, Cl$_3$CCH$_2$), 5.17 (2H, s, PhCH$_2$O), 5.66 (1H, s, 5—H), 6.75 (1H, br s, D$_2$O exch, NH) 7.34 (5H, s, phenyl), 7.70 (1H, brs, D$_2$O exch. NHCHO) and 8.19 1H, s, NHCHO).

EXAMPLE 11 t-Butyl 7α-formamido-7β-(2,2,2-trichloroethoxycarbonylamino)-cephalosporanate t-Butyl 7α-(methylthio)-7β-(2,2,2-trichloroethoxycarbonylamino)cephalosporanate (0.275 g, 0.05 mmol) in dimethylformamide (8 ml) containing N,N-bis(trimethylsilyl)formamide (0.190 g, 1 mmol) was treated with mercuric acetate (0.174 g, 0.55 mmol) in dimethylformamide (2 ml). The reaction mixture was poured into ethylacetate, washed successively with water, dilute sodium hydrogen carbonate solution, and brine, dried and evaporated. Chromatography on silica gel afforded the title compound (0.251 g). δ (CDCl$_3$)1.53 (9H, s, C(CH$_3$)$_3$), 2.07 (3H, s, OCOCH$_3$), 3.28 and 3.46 (2H, ABq, J17 Hz, 2—H$_2$), 4.7–5.3 (5H, m, 6—H, CH$_2$OAc, CH$_2$CCl$_3$), 6.66 (1H, s, NH), 7.63 (1H, br s, NH), 8.22 (1H, s, CHO); ν$_{max}$.(CH$_2$Cl$_2$), 3380, 1790, 1735, 1700 cm$^{-1}$.

EXAMPLE 12

(a) Benzyl 6-(N-2,2,2-trichloroethoxycarbonyl-N-trifluoromethanesulphonylamino)penicillanate Benzyl 6β-(trifluormethanesulphonyl)amino-penicillinate (2.58 g) [D. Hagiwara et al., J.C.S. Chem. Comm., 1982, 578; P.S.F. Mezes et al., Heterocycles, 19, 1982, 1207] was dissolved in dry dichloromethane (80 ml) at 0° C. and 2,2,2-trichloroethylchloroformate (2.5 g) and triethylamine (893 mg) were added, followed by 4-dimethylaminopyridine (72 mg). The cooling bath was removed. After 2 h the solution was poured into ethyl acetate. The solution was washed successively with dilute hydrochloric acid, water, dilute aqueous sodium hydrogen crbonate, brine, dried and evaporated. Chromatography on silica gel afforded the title compound (3.27 g). ν$_{max}$ (CHCl$_3$) 1795, 1785, 1745, 1420, 1130 cm$^{-1}$; δ(CDCl$_3$) 1.42 and 1.67 (6H, 2s (CH$_3$)$_2$C), 4.54 (1H, s, 3—H), 4.86 and 4.95 (2H, ABq, J 12 Hz), 5.20 (2H,AA′), 5.5 (1H,d,J4 Hz), 5.55(1H,d,J 4 Hz), 7.38(5H, s, aromatics).

(b) Benzyl 6β-(2,2,2-trichloroethoxycarbonylamino)-6α-formamidopenicillanate Benzyl 6-(N-2,2,2-trichloroethoxycarbonyl-N-trifluoromethanesulphonylamino)-penicillanate (613 mg) in dichloromethane (20 ml) was cooled to −5° C. and triethylamine (150 mg) and bis-(trimethylsilyl)formamide (378 mg; freshly distilled) were added. The cooling bath was removed. After one and three quarter hours the solution was poured into ethyl acetate and washed successively with dilute hydrochloric acid, brine, dried and evaporated. Chromatography on silica gel afforded the title compound (441 mg).

EXAMPLE 13

(a) t-Butyl 7β-(N-trifluoromethanesulphonylamino)cephalosporanate t-Butyl 7-aminocephalosporanate (3.28 g) in dichloromethane (100 ml) at −65° C. was treated successively with triethylamine (1.1 g) and trifluoromethanesulphonic anhydride (3.1 g). After 30 min. at −65° C., the reaction mixture was washed with dilute hydrochloric acid, followed by brine. The solution was dried and the solvent distilled off in vacuo to give the title compound (4.5 g) $\nu_{max}$ (Nujol) 1820, 1735, 1690, 1640 cm$^{-1}$; δ(CDCl$_3$), 1.52 (9H, s, C(CH$_3$)$_3$), 2.07 (3H, s, —OCOMe), 3.45 (2H, AA', S—CH$_2$), 4.87 and 5.05 (2H, ABq, J.13 Hz), 4.87 (1H, d, J5 Hz), 5.08 (1H d, J5 Hz), 6.5–8.5(1H, very broad s, exch. D$_2$O, —NH).

(b) t-Butyl 7β-(N-2,2,2-trichloroethoxycarbonyl-N-tri-fluoromethanesulphonylamino)cephalosporanate t-Butyl 7β-(N-trifluoromethanesulphonylamino)-cephalosporanate (920 mg) in dry dichloromethane (30 ml) was treated with triethylamine (222 mg) and 2,2,2-trichloroethylchloroformate (848 mg) for 48 h at room temperature. The solution was poured into ethyl acetate, and washed successively with dilute hydrochloric acid, water, dilute aqueous sodium hydrogen carbonate, and brine. The dried organic layer was evaporated and chromatographed on silica gel to give the title compound (1.05 g). $\nu_{max}$ (CHCl$_3$) 1795, 1780 sh, 1735 sh, 1720, 1420, 1150 cm$^{-1}$; δ(CDCl$_3$), 1.53 (9H, s, C(CH$_3$)$_3$), 2.08 (3H, s, OCOCH$_3$), 3.45 (2H, s, CH$_2$CO—), 4.82 and 5.13 (2H, ABq, J13 Hz), 4.99 (2H, AA' system), 5.08 (1H, d, J5 Hz), and 5.62 (1H, d, J5 Hz).

(c) t-Butyl 7β-(2,2,2-trichloroethoxycarbonylamino)-7α-formamidocephalosporanate

Method 1 t-Butyl 7β-(N-2,2,2-trichloroethoxylcarbonyl-N-trifluoromethanesulphonylamino)cephalosporanate (63 mg) in dichloromethane (2 ml) was cooled to −40° C. and bis-(trimethylsilyl)formamide (72 mg) added, followed by triethylamine (15 mg). The solution was warmed to −10° C. over 30 min. After a further 30 min. at 0/−5° C. the solution was poured into ethyl acetate, washed successively with dilute hydrochloric acid and brine, dried and evaporated. Chromatography on silica gel gave the title compound (30 mg), containing ca 5% of delta-2 isomer.

Method 2 t-Butyl 7β-(N-2,2,2-trichlorethoxycarbonyl-N-trifluoromethanesulphonylamino)cephalosporanate (63 mg) in dichloromethane (2 ml) was treated with bis-(trimethylsilyl)formamide (76 mg) and triethylamine (11 mg). After 16 h at room temperature the solution was worked up as in Method 1. Chromatography on silica gel afforded the product (48 mg) which consisted of the title compound (20%) and t-butyl 3-acetoxymethyl 7β-(2,2,2-trichloroethoxycarbonylamino)-7α-formamidoceph-2-em-4-carboxylate (80%). The latter showed inter alia δ(CDCl$_3$) 1.45 (9H, s, C(CH$_3$)$_3$), 2.08 (3H, s, —OCOCH$_3$), 4.92 (1H, slightly broadened s, 4—H), 5.42 (1H, s, 6—H), 6.3 (1H, slightly broadened s, 2—H).

The mixture of Δ-2 and Δ-3 isomers (48 mg) was dissolved in ethylacetate (2 ml) at −10° C. and m-chloroperbenzoic acid (16 mg) added. After 15 min. the solution was washed with dilute aqueous sodium hydrogen carbonate and brine, dried and evaporated. The residue was dissolved in methanol. After 30 min. the solvent was evaporated off and the residue dried in vauco. The product was dissolved in dichloromethane (2 ml) at 0° C. and phosphorus trichloride (36 mg) added. After 45 min the solution was poured into ethyl acetate and washed successively with dilute aqueous sodium hydrogen carbonate and brine. The organic layer was dried and evaporated. Chromatography on silica gel afforded t-butyl 7β-(2,2,2-trichloroethoxycarbonylamino)-7α-formamidocephalosporanate (25 mg).

Method 3 t-Butyl 7β-(N-2,2,2-trichloroethoxycarbonyl-N-trifluoromethanesulphonylamino)cephalosporanate (63 mg) in dichloromethane (2 ml) at −60° C. was treated with bis-(trimethylsilyl)formamide (76 mg) and 1,8-diazabicyclo[5.4.0]undec-7-ene (DBU) (20 mg). The temperature was allowed to reach −5° C. After 30 min at this temperature the reaction mixture was worked up as in Method 1. Chromatography on silica gel gave the product which contained some of the title compound, but was mainly t-butyl 3-acetoxymethyl-7β-(2,2,2-trichloroethoxycarbonylamino)-7α-formamido-ceph-2-em-4-carboxylate. The latter was converted into the title compound by the oxidation/reduction sequence described in Method 2 of this example.

EXAMPLE 14

(a) t-Butyl 7β-(N-2,2,2-trichloroethoxycarbonyl-N-trifluoromethanesulphonylamino)cephalosporanate-1α-oxide t-Butyl 7β-(N-2,2,2-trichloroethoxycarbonyl-N-trifluoromethanesulphonylamino)cephalosporanate (648 νmg) was dissolved in ethyl acetate (20 ml) at −10° C. and m-chloroperbenzoic (193 mg; 90% pure) added. The solution was washed with dilute aqueous sodium hydrogen carbonate, brine, dried and evaporated. Chromatography on silica afforded the title compound (466 mg). $\nu_{max}$ (CHCl$_3$) 1810, 1750, 1730, 1425, 1150, 1035 cm$^{-1}$; δ(CDCl$_3$) 1.53 (9H, s, C(CH$_3$)$_3$), 2.08 (3H, s, —OCOCH$_3$), 3.48 and 3.99 (2H, ABq, J 16 Hz, SCH$_2$), 4.6 (1H, d, J5 Hz), 4.84 and 5.19 (2H, ABq, J 14 Hz), 4.91 (2H, AA'), 5.87 (1H, d, J 5 Hz).

(b) t-Butyl 7β-(2,2,2-trichloroethoxycarbonylamino)-7α-formamidocephalosporanate-1α-oxide t-Butyl 7β-(N-2,2,2-trichloroethoxycarbonyl-N-trifluoromethanesulphonylamino)cephalosporanate-1α-oxide (64 mg) in dichloromethane (2 ml) was treated with bis-(trimethylsilyl)formamide (72 mg) and triethylamine (10 mg). After 10 min. the solution was diluted with ethyl acetate, washed successively with dilute hydrochloric acid, water, dilute aqueous sodium hydrogen carbonate and brine, dried and evaporated. Chromatography on silica gel gave the title compound (15 mg). $\nu_{max}$ (CHCl$_3$) 3480, 3200br, 1805, 1730, 1700 sh, 1040 cm$^{-1}$; δCDCl$_3$) 1.6 (9H,s,C(CH$_3$)$_3$), 2.13 (3H,s, OCOCH$_3$), 3.47 and 4.0 (2H, ABq, J 16 Hz, SOCH$_2$), 4..67 (2H, AA'), 4.5–5.1 (3H, m), 7.4 (1H, bs, exch. D$_2$O) 8.07 (2H, s, 1H exch. D$_2$O).

Reduction of this material as described in Example 13(c) (Method 2) gave t-butyl 7β-(2,2,2-trichloroethoxycarbonylamino)-7α-formamidocephalosporanate.

EXAMPLE 15 t-Butyl 7β-(t-butoxycarbonylamino)7α-formamidocephalosporanate t-Butoxycarbonyl azide (312 mg) was dissolved in dichloromethane (10 ml) and triphenylphosphine (573 mg) added cautiously in dichloromethane (10 ml). After 10 min. t-butyl 7-oxocephalosporanate (715 mg) (D. Hagiwara et al., *J.C.S. Chem. Comm.*, 1982, 578) was added, followed by further t-butyl 7-oxocephalosporanate (82 mg) after 2 h. After a further 2 h. bis-(trimethylsilyl)formamide (826 mg) was added.

After 1 h the reaction mixture was diluted with ethyl acetate and washed with water. The organic layer was separated, washed with dilute hydrochloric acid, brine, dried and evaporated. Chromatography on silica gel gave the title compound (650 mg). $v_{max}$ (CHCl$_3$) 3420, 1790, 1720 br cm$^{-1}$; δ(CDCl$_3$) 1.47 (9H, s, C(CH)$_3$)$_3$), 1.53 (9H, s, C(CH$_3$)$_3$), 2.05 (2H, s, OCOCH$_3$), 3.22 and 3.5 (2H, ABq, J 17 Hz, SCH$_2$), 4.72 and 5.06 (2H, ABq, J 14 Hz, —CH$_2$OCO—), 5.15 (1H, s, 6—H), 5.91 (1H, slightly broadened s, exch. D$_2$O,NH), 7.42 (bs, 1H, exch. D$_2$O), 8.21 (s, 1H, CHO).

EXAMPLE 16

(a) Benzyl 6-(N-2,2,2-trichloroethoxycarbonyl-N-trifluoromethanesulphonylamino)penicillanate-1α-oxide Benzyl 6-(N-2,2,2-trichloroethoxycarbonyl-N-trifluoromethanesulphonylamino)penicillanate (613 mg) was dissolved in dry dichloromethane (10 ml) at $-10°$ C. and peracetic acid (1.5 ml of 5.24% solution in acetic acid) was added. After 16 hour at 0° C. the solvent was evaporated in vacuo. After addition of toluene and repetition of the evaporation (three times), the residue was chromatographed on silica gel to give the title compound (516 mg). $v_{max}$ (CHCl$_3$) 1810, 1755, 1425, 1130 cm$^{-1}$; δ(CDCl$_3$) 1.18 and 1.68 (6H,2s, (CH$_3$)$_2$C), 4.45 (1H,s,3—H), 4.73 (1H,d,J 4.5 Hz), 4.81 and 4.97 (2H,ABq, J 12 Hz), 5.21(2H,AA'), 5.7 (1H,d,J 4.5 Hz), 7.35 (5H,s, aromatics).

(b) Benzyl 6β-(2,2,2-trichloroethoxycarbonylamino)-6α-formamido penicillanate-1α-oxide Benzyl 6-(N-2,2,2-trichloroethoxycarbonyl-N-trifluoromethanesulphonylamino)penicillanate-1α-oxide (63 mg) was dissolved in dry dichloromethane (2 ml) at $-10°$ C. and bis-(trimethylsilyl)formamide (40 mg) was added, followed immediately by triethylamine (10 mg). The temperature was allowed to rise to $-5°$ C. and after 40 minutes the solution was poured into ethyl acetate and washed successively with dilute hydrochloric acid, brine, dried and evaporated. Chromatography on silica gel afforded the title compound (41 mg); $v_{max}$ (CHCl$_3$) 3200 (broad), 1800, 1740, 1700 cm$^{-1}$; δ(CDCl$_3$) 1.25 and 1.48 (6H, 2s, (CH$_3$)$_2$C), 4.56(1H,s,3—H), 4.68 and 4.89 (2H, ABq, J13 Hz), 5.16 (1H,s,), 5.2 (2H,AA') 7.2b(1H,s,exch.D$_2$O) 7.33 (5H,s, aromatics), 8.03b(1H,s, exchD$_2$O), 8.17 (1H,s, C$\underline{H}$O).

EXAMPLE 17

(a) Benzyl 6β-(trifluoromethanesulphonyl)aminopenicillanate-1β-oxide

Benzyl 6β-(trifluoromethanesulphonyl)aminopenicillanate (3.12 g) was dissolved in dry dichloromethane (50 ml) at $-10°$ C. and peracetic acid (1 ml of 52.4% solution in acetic acid) added. After 15 minutes the solvent was evaporated. After addition of toluene and repetition of the evaporation (three times), the residue was chromatographed on silica gel to give the title compound (2.6 g); $v_{max}$ (CHCl$_3$) 3250, 1810, 1750, 1440, 1140 cm$^{-1}$; δ(CDCl$_3$) 1.05 and 1.64(6H,2s,(CH$_3$)$_2$C), 4.69(1H,s,3H), 4.98(1H,d,J 4.5 Hz), 5.1 and 5.28(2H,ABq,J12 Hz), 5.31 (1H,d,J 4.5 Hz), 7.34 (5H,s,aromatics). Triflate N$\underline{H}$ too broad to observe.

(b) Benzyl 6-(N-2,2,2-trichloroethoxycarbonyl-N-trifluoromethanesulphonylamino)penicillanate-1β-oxide Benzyl 6β-(trifluoromethanesulphonyl) aminopenicillanate-1β-oxide (988 mg) was dissolved in dry dichloromethane (30 ml) at $-10°$ C. and trichloroethylchloroformate (844 mg) added, followed by pyridine (240 mg). The temperature was raised to 0° C. and after 1½ hour the reaction mixture was poured into ethyl acetate/dilute hydrochloric acid. The organic layer was separated, washed with brine, dried and evaporated. Chromatography on silica gel gave the title compound (1.14 g); $v_{max}$ (CHCl$_3$) 1750, 1420, 1125, 1045 cm$^{-1}$; δ(CDCl$_3$) 1.05 and 1.6 (6H, 2s, (CH$_3$)$_2$C), 4.7 (1H,s,3—H), 4.88(2H,AA'), 5.01(1H,d,J5 Hz) 5.13 and 5.3(2H,ABq,J12 Hz), 5.52 (1H,s,J5 Hz), 7.34(5H,s,aromatics).

(c) Benzyl 6β-(2,2,2-trichloroethoxycarbonylamino) 6α-formamidopenicillanate-1β-oxide Benzyl 6-(N-2,2,2-trichloroethoxycarbonyl-N-trifluoromethanesulphonylamino)penicillanate-1β-oxide (126 mg) was dissolved in dry dichloromethane (3 ml) at $-10°$ C. and bis-(trimethylsilyl)formamide (80 mg) was added, followed immediately by triethylamine (20 mg). After 20 min at $-10°$ C./$-5°$ C. the solution was poured into ethyl acetate, and washed with dilute hydrochloric acid, followed by brine, dried and evaporated. Chromatography on silica gel afforded the title compound (81 mg); $v_{max}$(CHCl$_3$) 3400, 3250, 1795, 1735(broad), 1700, 1050 cm$^{-1}$; δ(CDCl$_3$) 1.06 and 1.6 (6H,2s, (CH$_3$)$_2$C)4.68(1H,s,3—H), 4.72 (2H,AA'), 5.2(1H,s), 5.13 and 5.32(2H,ABq,J12 Hz), 7.35(5H,s,aromatics), 7.45b (1H,s,exch. D$_2$O), 8.22(1H,s,CHO). One N$\underline{H}$ obscured by other peaks.

EXAMPLE 18

(a) t-Butyl 7β-(N-pentafluorophenylsulphonylamino) cephalosporanate t-Butyl 7-aminocephalosporanate (371 mg) was dissolved in dry dichloromethane (4 ml) at $-20°$ C. and pentafluorophenylsulphonyl chloride (305 mg) added, followed by pyridine (86 mg). After 30 minutes the cooling-bath was removed and the solution left at room temperature for 21 hour. The solution was diluted with ethyl acetate and washed successively with dilute hydrochloric acid, aqueous sodium hydrogen carbonate and brine, dried and evaporated. Chromatography on silica gel eluting with ethyl acetate-dichloromethane mixtures gave the title compound (332 mg); m.p. 204°–205° C. (ethyl acetate-hexane); $\nu_{max}$ (Nujol) 3100, 1810, 1730, 1700, 1640, 1460, 1160, 980 cm$^{-1}$; δ(CDCl$_3$) 1.48 (9H,s,C(Me)$_3$)2.03 (3H,s,OCOCH$_3$), 3.3 and 3.57 (2H,ABq,J18 Hz, S—CH$_2$), 4.75 and 5.09 (2H, ABq,J14 Hz,CH$_2$OCO), 4.93 (1H,d,J5 Hz), 5.4(1H, slightly broadened, d,J5 Hz, 7—H), 6.4b(1H,s,exch D$_2$O). (Found: C,43.1; H, 3.7; N,4.7; S 11.3 C$_{20}$H$_{19}$N$_2$O$_7$S$_2$F$_5$ requires C,43.0; H,3.4; N,5.0; S,11.5%).

(b) Butyl 7β-(N-pentafluororphenylsulphonyl-N-2,2,2-trichloroethoxycarbonylamino) cephalosporanate t-Butyl 7β-(N-pentafluorophenylsulphonylamino) cephalosporanate (246 mg) was dissolved in dichloromethane (10 ml) at −20° C. and trichloroethylchloroformate (186 mg) added followed by pyridine (52 mg). The solution was diluted with dichloromethane, washed with dilute hydrochloric acid followed by brine, dried and evaporated. Chromatography on silica gel gave the title compound (320 mg) as a white solid after trituration with ether hexane; $\nu_{max}$(CHCl$_3$) 1790, 1730(broad), 1735, 1500 1160, 990 cm$^{-1}$; δ(CDCl$_3$) 1.53 (9H,s, (CH$_3$)$_3$),2.04(2H,s,OCOCH$_3$), 3.42(2H,AA′), 4.77(2H,AA′) 4.77 and 5.05(2H,ABq,J13 Hz), 5.08 (1H,d,J5 Hz), 5.96(1H,d,J5 Hz).

(c) t-Butyl 7β-(2,2,2-trichloroethoxycarbonylamino)-7α-formamidocephalosporanate t-Butyl 7β-(N-pentafluorophenylsulphonyl-N-2,2,2-trichloroethyoxycarbonylamino)cephalosporanate (63 mg) was dissolved in dry dichloromethane at −10° C. and bis-(trimethylsilyl)formamide (37 mg) was added, followed immediately by triethylamine (15 mg). The cooling-bath was removed and the solution kept at room temperature for 2 hour. The solvent was evaporated and the residue chromatographed on silica gel to give a mixture (12 mg) of the title compound (15%) and t-butyl 3-acetoxymethyl-7β-(2,2,2-trichloroethoxycarbonylamino)-7α-formamido-ceph-2-em-4-carboxylate (85%).

EXAMPLE 19

(a) t-Butyl 7β-(N-2,4-dinitrophenylsulphonyl)amino cephalosporanate t-butyl 7-aminocephalosporanate (742 mg) dissolved in dry dichloromethane (15 ml) at −10° C. was treated with pyridine (173 mg) and 2,4-dinitrophenylsulphonyl chloride (588 mg). The cooling-bath was removed. The solution stirred at room temperature for 16 h, then poured into ethyl acetate, and washed successively with dilute hydrochloric acid, brine, dilute aqueous sodium hydrogen carbonate, brine (×2), dried and evaporated. Chromatography of the residue on silica gel eluting with ethyl acetate-dichloromethane mixtures gave the title compound (588 mg); $\nu_{max}$(Nujol) 3225, 3090, 1795, 1730, 1710, 1738, 1535, 1450, 1365, 1170 cm$^{-1}$ ; δ(CDCl$_3$30 [CD$_3$]$_2$SO) 1.49 (9H,s,(CH $_3$)$_3$C), 2.02 (3H, s, OCOCH$_3$), 3.12 and 3.48 (2H, ABq, J 18 Hz), 4.72 and 5.03 (2H, ABq, J 13 Hz, 4.96 (1H, d, J 4.5 Hz) 5.38 (1H, d, J 4.5 Hz), 8.4–8.65 (3H, m, aromatics). SO$_2$NH is very broad and not clearly visible.

(b) t-butyl 7β-(N-2,4-dinitrophenylsulphonyl-N-2,2,2-trichloroethoxycarbonylamino)cephalosporanate t-Butyl 7β-(N-2,4-dinitrophenylsulphonylamino) cephalosporanate (279 mg) in dry dichloromethane (10 ml) at −5° C. was treated with trichloroethylchloroformate (211 mg) and pyridine (44 mg). The solution was diluted with ethylacetate, washed with dilute hydrochloric acid, followed by brine, dried and evaporated. Chromatography on silica gel gave the title compound. $\nu_{max}$ (CHCl$_3$) 1790, 1738, 1730, 1545, 1345, 1170, 1150 cm$^{-1}$; δ(CDCl$_3$) 1.55 (9H, s, (CH$_3$)$_2$C), 2.09 (3H, s, OCOCH$_3$), 3.40 and 3.57 (2H, ABq, J 17.9 Hz), 4.72 and 4.81 (2H, ABq, J 11.8 Hz), 4.80 and 4.99 (2H, ABq, J 13 Hz), 5.2 (1H, d, J 5.1 Hz), 5.99 (1H, d, J 5.1 Hz) 8.59–8.76 (3H, m, aromatics).

(c) t-Butyl 7β-(2,2,2-trichloroethoxycarbonylamino)-7α-formamidocephalosporanate t-Butyl 7β-(N-2,4-dinitrophenylsulphonyl-N-2,2,2-trichloroethoxycarbonylamino)cephalosporanate (122 mg) in dry dichloromethane (3 ml) at −10° C. was treated with bis-trimethylsilyformamide (96 mg) and triethylamine (25 mg). The cooling bath was removed and the solution stirred at room temperature for 4½ h. Ethyl acetate was added and the solution washed with dilute hydrochloric acid, followed by brine, dried and evaporated. Chromatography on silica gel gave a mixture (37 mg) of the title compound (40%) and t-butyl 3-acetoxymethyl-7β-(2,2,2-trichloroethoxycarbonylamino)-7α-formamido-ceph-2-em-4-carboxylate (60%).

EXAMPLE 20

Benzyl 6α-formamido-6β-(phenylacetamido)penicillanate (a) A solution of benzyl 6α-methylsulphinyl-6β-(phenylacetamido)-penicillanate (52 mg, 0.107 mmol) in dry dichloromethane (5 ml) and bis-(trimethylsilyl)formamide (40.4 mg, 0.214 mmol) was treated with triethylamine (11.9 mg, 0.118 mmol, 16.4 μl) for 19 h at room temperature. The mixture was then diluted with dichloromethane (15 ml) and washed successively with dilute aqueous hydrochloric acid, dilute aqueous sodium hydrogen carbonate and saturated brine. The solution was then dried (MgSO$_4$) and evaporated to afford the title compound (24 mg, 48%); (see UK Patent Application, No. GB2107307A).

(b) A solution of benzyl 6α-methylsulphinyl-6β-(phenylacetamido)penicillanate (70 mg, 0.144 mmol) in dry tetrahydrofuran (10 ml) and bis-(trimethylsilyl)-formamide (54.4 mg, 0.288 mmol) was heated under reflux for 3.5 h and then allowed to stand at room temperature for 18 h. The solvent was then evaporated in vacuo and the residue taken up in ethyl acetate (20 ml). The solution was washed successively with 2N-hydrochloric acid (15 ml), saturated aqueous sodium hydrogen carbonate (10 ml) and saturated brine (10 ml), dried (MgSO$_4$) and evaporated. The yellow gum so obtained was chromatographed on silica gel to give the title compound (61 mg, 91%).

EXAMPLE 21

Benzyl 6α-formamido-6β-(phenylacetamido)penicillanate-1β-oxide

A solution of benzyl 6α-methylsulphinyl-6β-(phenylacetamido)penicillanate-1β-oxide (80 mg, 0.159 mmol) in dry tetrahydrofuran (5 ml) and bis-(trimethylsilyl)formamide (120 mg, 0.635 mmol) was heated under reflux for 6 h and then allowed to stand at room temperature for 18 h. The solvent was then evaporated in vacuo and the residue taken up in ethyl acetate (15 ml). The solution was washed successively with 2N-hydrochloric acid (10 ml) and saturated brine (10 ml), dried (MgSO$_4$) and evaporated. Chromatography of the crude product on silica gel gave the title compound (30 mg, 39%) $\nu_{max}$(CHCl$_3$) 3250, 2930, 1795, 1745, and 1680 cm$^{-1}$, δ(CDCl$_3$) 1.01 and 1.56 (3H,s), 3.53 (2H,s), 4.72 (1H,s), 5.08 (1H,s), 5.24 (2H, ABq, J 12 Hz), 7.26 (5H,s), 7.37 (5H,s), 7.78 (1H, br s), 7.90 br (1H, s) and 7.99 and 8.33 (together 1H each s), (addition of D$_2$O caused the signals at 7.78 and 7.90 to disappear).

EXAMPLE 22

Benzyl 6α-formamido-6β-[D-2-phenyl-2-(2,2,2-trichloroethoxycarbonylamino)acetamido] penicillanate Benzyl 6α-methylthio-6β-[D-2-phenyl-2-(2,2,2-trichloroethoxycarbonylamino)acetamido]penicillanate (3.30 g, 5 mmol) and N,N-bis(trimethylsilyl)formamide (2.2 ml, 10 mmol) in N,N-dimethylformamide (30 ml) was treated with silver acetate (0.840 g, 5 mmol) and stirred at room temperature for 0.5 h. The reaction mixture was diluted with ethyl acetate and water and then filtered through Celite. The two phases of the filtrate was separated and the ethyl acetate layer was washed with water and brine before being dried over magnesium sulphate. The solution was filtered and evaporated to dryness to yield the crude product as a white foam (3.23 g). This was chromatographed on silica gel 60 (<230 mesh ASTM) (120 g) eluting with 2:1 hexane/ethyl acetate grading to 1:1 hexane/ethyl acetate to yield the title compound as a white foam (1.70 g, 2.6 mmol, 52% yield); $\nu_{max}$(CH$_2$Cl$_2$) 3500 sh, 3410, 3300, 1790, 1745, 1695, 1495, 1205 cm$^{-1}$; δ(CDCl$_3$) 0.98 and 1.28 (6H, 2s, C(CH$_3$)$_2$), 4.38 (1H,s, 3—H), 4.57, 4.73 (2H, ABq, J 13 Hz, CH$_2$CCl$_3$), 5.13 (2H,s, CH$_2$Ph), 5.45–5.72 (2H, m, NHCHCO, 5—H), 6.82 (1H, d, J 7 Hz, NHCH), 7.10–7.62 (10H, m, aromatics), 7.88 (1H, s, NH), 8.09 (1H, s, NHCHO), and 8.55 (1H, s, NH). (Found: MH$^+$, 657. C$_{27}$H$_{27}$Cl$_3$N$_4$O$_7$S requires M, 656).

EXAMPLE 23

Benzyl 6β-[D-2-[(4-n-butyl-2,3-dioxopiperazin-1-yl)carbonylamino]-2-phenylacetamido]-6α-formamidopenicillanate Benzyl 6β-[D-2-[(4-n-butyl-2,3-dioxopiperazin-1-yl)carbonyl-amino]-2-phenylacetamido]-6α-(methylthio)-penicilllanate (400 mg; 0.59 mMole) in tetrahydrofuran (5 ml) was treated at room temperature with mercuric acetate (187 mg; 0.59 mMole) then N,N-bis-(trimethylsilyl)formamide (218 mg; 1.2 mMole). It was stirred at room temperature for 0.5 h, diluted with ethyl acetate (25 ml) and filtered through Dicalite. The filtrate was washed with water (25 ml), saturated brine (25 ml), dried over anhydrous magnesium suphate and evaporated to dryness in vacuo to yield a yellow foam. Chromatography on silica gel 60(<230 mesh ASTM), eluting with 50% ethyl acetate in cyclohexane, gave the title compound (76 mg; 19% yield) as a white foam, $\nu_{max}$ (tetrahydrofuran) 1785, 1740, and 1693 cm$^-$; δ[CD$_3$)$_2$CO] 0.92 and 1.16 (6H, 2s, 2-C(CH$_3$)$_2$), 0.93 (3H, t, J8 Hz, (CH$_2$)$_2$CH$_3$), 1.24–1.45 and 1.52–1.69 (4H, 2m, NCH$_2$(CH$_2$)$_2$CH$_3$), 3.40–3.53, 3.62–3.74 and 3.95–4.08 (6H, 3m, N(CH$_2$)$_2$NCH$_2$), 4.39 (1H, s, 3—H), 5.12–5.28 (2H, m, CH$_2$Ph), 5.58 (1H, s, 5—H), 5.62–5.73 (1H, m, CHCO), 7.25–7.63 (10H, 2m, aromatics), 8.18 (1H, d, J2 Hz, CHO), 8.23 (1H, brs, NHCHO), 8.77 (1H, brs, CONH), 10.04 (1H, d, J7 Hz, NHCHCO).

EXAMPLE 24

(a) Benzyl 6β-[D-2-[(4-ethyl-2,3-dioxopiperazin-1-yl)-carbonylamino]-2-[4-(benzyloxycarbonyloxy)phenyl]acetamido]-6α-formamidopenicillanate A solution of benzyl 6α-[D-2-[(4-ethyl-2,3-dioxopiperazin-1-yl)carbonylamino]-2-[4-benzyloxy carbonyloxy)phenyl]acetamido]-6α(methylthio) penicillanate (2.01 g, 2.5 mmol) and N,N-bis(trimethylsilyl)formamide (0.95 g, 5 mmol) in N,N-dimethylformamide (30 ml) under argon, was treated with a solution of mercuric acetate (0.80 g, 2.5 mmol) in N,N-dimethylformamide over 10 minutes. The resulting solution was stirred at room temperature for 4 h, before being poured into ethyl acetate (150 ml) and washed with water (5×100 ml) and brine (50 ml). The organic solution was dried over magnesium sulphate and then evaporated to dryness to leave a pale yellow glass. This was purified by chromatography on silica gel 60 eluting with ethyl acetate grading to 5% ethanol/ethyl acetate, to afford the title compound 1.17 g, 59%). $\nu_{max}$ (CH$_2$Cl$_2$) 3275, 1790, 1770, 1750, 1725, 1715, 1695, 1682 sh, 1500, 1210 cm$^{-1}$; δ[(CD$_3$)$_2$CO] 0.97 and 1.18 (6H, 2s, gem dimethyls), 1.17 (3H, t, J7 Hz, CH$_2$CH$_3$), 3.48 (2H, q, J7 Hz, CH$_2$CH$_3$), 3.65 (2H, m, piperazine CH$_2$), 4.00 (2H, m, piperazine CH$_2$), 4.39 (1H, s, 3—H), 5.18 (2H, s, ester CH$_2$), 5.26 (2H, s, carbonate CH$_2$) 5.58 (1H, s, 5—H), 5.73 (1H, d, J7 Hz, collapses to singlet on D$_2$O exchange, α-proton), 7.10–7.70 (14H, m, aromatics), 8.16 (1H, s, NHCHO), 8.23 (1H, s, exchangeable with D$_2$O, NHCHO), 8.88 (1H, d, exchangeable with D$_2$O, 6β-amido proton), and 10.05 (1H, s, J7 Hz, exchangeable with D$_2$O α-amido proton).

(b) 6β-[D-2-[(4-Ethyl-2,3-dioxopiperazin-1-yl) carbonylamino]-2-(4-hydroxyphenyl)acetamido]-6α-formamidopenicillanic acid, sodium salt A solution of benzyl 6β-[(D-2-[4-ethyl-2,3-dioxopiperazin-1-yl)carbonylamino]-2-[4-(benzyloxycarbonyloxy)phenyl]acetamido]-6α-formamidopenicillanate (0.50 g, 0.625 mmol) in tetrahydrofuran (15 ml) was added to a suspension of 10% palladium on charcoal (0.50 g) in ethanol (15 ml) and water (1 ml) which had been pre-hydrogenerated for 0.5 h. The mixture was then hydrogenated for 45 minutes, and the catalyst was filtered and washed with dilute sodium bicarbonate solution. The filtrate was then washed with ethyl acetate, saturated with sodium chloride and acidified to pH 1.5 before extraction of the product into tetrahydrofuran/ethyl acetate (50:50). The combined extracts were washed with brine, dried over magnesium sulphate and evaporated to leave the free acid as a white solid (0.25 g). This was suspended in water and the pH carefully adjusted from 2.0 to 7.0 by addition of dilute sodium bicarbonate solution. The resulting solution was filtered and freeze dried to afford the title penicillin (256 mg, 69%). Hplc showed one major peak, $\nu_{max}$ (KBr) 1770, 1710, 1685, 1670, 1610, 1510 cm$^{-1}$ $\delta$(D$_2$O) 0.95 and 1.33 (6H, 2s, gem dimethyls), 1.21 (3H, t, J7 Hz CH$_2$CH$_3$) 3.50 (2H, q, J7 Hz, CH$_2$CH$_3$), 3.65 (2H, m, piperazine CH$_2$), 3.98 (2H, m, piperazine CH$_2$) 4.16 (1H, s, 3—H) 5.37 (1H, s, 5—H) 5.59 (1H, s, α-proton), 6.86 and 7.35 (4H, AA'BB', J9 Hz, aromatics) and 8.00 (1H, s, NHCHO). MIC against *P.mirabilis* 889 is 0.1 μg/ml.

EXAMPLE 25

Benzyl 6β-(phenoxyacetamido)-6α-formamidopenicillanate

Benzyl 6β-(phenoxyacetamido)-6α-(methylthio)penicillanate (0.49 g, 1 mmol) was dissolved in dry dimethylformamide (8 ml) and cooled to −40° C. under argon with stirring. Silver (I) acetate (0.25 g, 1.5 mmol) was added, following by N-hydroxysuccinimide (0.17 g, 1.5 mmol). Stirring was continued while the mixture regained room temperature. After 1.5 h the mixture was partitioned between ethyl acetate (40 ml) and water (40 ml). The organic phase was separated and washed further with water (4×40 ml), then with brine, dried over anhydrous magnesium sulphate and evaporated to give a foam. Without further purification, this material was redissolved in dry tetrahydrofuran (5 ml), cooled to 0° C. and stirred under argon. Bis(trimethylsilyl)formamide (0.48 ml, 2.5 mmol) was then added, followed quickly by triethylamine (0.28 ml, 2 mmol). The resulting solution was allowed to regain room temperature, and after 1 h was partitioned between ethyl acetate (20 ml) and 0.5M hydrochloric acid (2×20 ml). The organic solution was washed further with saturated aqueous sodium hydrogen carbonate (2×20 ml), water and brine, then dried over anhydrous magnesium sulphate. Evaporation gave crude product (0.47 g), which was chromatographed on silica gel (230–400 mesh, 50 g), eluting with 5% methanol in chloroform. Appropriate fractions were combined and evaporated to afford the 6α-formamidopenicillin (0.38 g, 78%), R$_f$0.4 in 10% methanol-chloroform; $\nu_{max}$ (KBr), 1787, 1744, 1688, 1599, 1589 and 1492 cm$^{-1}$; $\delta$(CDCl$_3$) 1.35; 1.37 (6H, 2s, 2—CH$_3$'s), 4.51 (1H, s, 3—H), 4.52 (2H, s, OCH$_3$CO), 5.19 (2H, ABq, ArCH$_2$O) 5.73 (1H, s, 5—H), 6.9–7.1 (3H, m, ArH), 7.2–7.5 (8H, m, ArH+NH), 8.01 (1H, br, s, D$_2$O exchanged, NHCHO) 8.21 (1H, v narrowed, s on D$_2$O exchange, NHCHO).

EXAMPLE 26

Benzyl 6β-[D-2-[(4-Ethyl-2,3-dioxopiperazin-1-yl)carbonylamino]-2-phenylacetamido]-6α-formamidopenicillanate Benzyl 6β-(D-2-[(4-ethyl-2,3-dioxopiperazin-1-yl)carbonylamino]-2-phenylacetamido]-6α-(methylthio)penicillate (1.63 g, 2.5 mmol) was dissolved in dry dimethylformamide (40 ml). The solution at room temperature was stirred under argon. Mercury (II) acetate (0.80 g, 2.5 mmol) was added in one portion, followed rapidly by bis(trimethylsilyl)formamide (0.95 ml, 5 mmol). After 1 h the reaction mixture, which showed no starting material by t.l.c., was partitioned between ethyl acetate (150 ml) and water (100 ml). The organic phase was separated and washed further with water (4×100 ml) and brine (50 ml), then dried over anhydrous magnesium sulphate. Evaporation gave crude product (1.48 g), which was subjected to chromatography on silica gel (230–400 mesh, 148 g) eluting with 2.5% methanol in chloroform. Appropriate fractions were pooled and evaporated to give the title 6α-formamidopenicillin (0.95 g, 59%); R$_f$0.31 in 10% methanol-chloroform; $\nu_{max}$ (KBr) 1785, 1740 sh, 1715, 1685, and 1500 cm$^{-1}$; $\delta$[(CD$_3$)$_2$CO] 1.13, 1.23, (6H, 2s, 2—CH$_3$'s), 1.13 (3H, t, NCH$_2$CH$_3$), 3.3–3.75 (4H, m, 2 NCH$_2$'s) 3.97 (2H, m, NCH$_2$), 4.33 (1H, s, 3—H), 5.13 (2H, s, ArCH$_2$O), 5.20 L (1H, s, 5—H), 5.57 (1H, d, CHN), 7.1–7.6 (10H, m, ArH), 8.12 (1H, s, NHCHO). The NH signals were already appreciably broadened by exchange with solvent H$_2$O; on D$_2$O exchange the $\delta$5.57 signal became a singlet and the $\delta$8.12 signal sharpened.

EXAMPLE 27

(a) Benzyl 6β-(Nonafluorobutanesulphonylamino)penicillanate

Benzyl 6-aminopenicillanate (ex. benzyl 6-aminopenicillanate, p-toluene sulphonic acid salt (466 mg; 0.97 mmol)) was dissolved in anhydrous MDC (5 ml), cooled to −60° under argon and triethylamine (109 mg; 1.06 mmol) added, followed by nonafluorobutanesulphonic acid anhydride (624 mg; 1.06 mmol). The reaction mixture was allowed to warm to 0° over 1 h, diluted with ethyl acetate and washed with dilute hydrochloric acid, saturated sodium hydrogencarbonate solution, brine, dried (MgSO$_4$) and evaporated. Chromatography of the residue gave two products, benzyl 6β-(N,N-bis-nonfluorobutanesulphonylamino)penicillanate (54 mg; 6%). $\nu_{max}$(CHCl$_3$) 1795, 1750, 1390, 1140 cm$^{-1}$; $\delta$ppm (CDCl$_3$) 1.44 (3H,s), 1.63 (3H,s), 4.52 (1H,s), 5.20 (2H,s), 5.26 (1H,d,J 4.2 Hz), 5.58 (1H,d,J 4.2 Hz), 7.37 (5H,s) and the title product (130 mg; 23%) $\nu_{max}$ (CHCl$_3$) 3345, 1795, 1745, 1390, 1140 cm$^{-1}$; $\delta$ppm (CDCl$_3$) 1.44 (3H,s), 1.63 (3H,s), 4.52 (1H,s), 5.20 (2 H,s), 5.26 (1H,d,J 4.2 Hz), 5.58 (1H,d,J 4.2 Hz), 7.38 (5 H,s). (Found: M$^+$, 588.0441, C$_{19}$H$_{17}$N$_2$O$_5$S$_2$F$_9$ requires M 588.0436).

(b) Benzyl 6β-(N-2,2,2-trichloroethoxycarbonyl-N-nonafluorobutanesulphonyl-amino)-penicillanate Benzyl 6β-(nonafluorobutanesulphonylamino)penicillanate (169 mg; 0.287 mmol) was dissolved in dry MDC (5 ml), cooled to 0° C. and trichloroethylchloroformate (121 mg; 0.594 mmol), triethylamine (44 mg; 0.43 mmol), and 2-N,N-dimethylaminopyridine (3.5 mg; 0.029 mmol) added successively. The reaction mixture was removed from the cooling bath, stirred for 2 h, and poured into ethyl acetate. The organic phase was washed with dilute hydrochloric acid, dilute sodium hydrogencarbonate, brine, dried (MgSO$_4$) and evaporated. Chromatography on silica gel afforded the title product (121 mg; 55%) $\nu_{max}$ (CHCl$_3$) 1798, 1978, 1740, 1350, 1140 cm$^{-1}$; $\delta$ppm (CDCl$_3$) inter alia 1.43 (3H,s), 1.69 (3H,s), 4.57 (1H,s), 4,85 and 4.95 (2H, ABq, J 11.7 Hz), 5.19 (2H, AA'), 5.54 (2H,s), 7.38 (5H,s).

Benzyl 6α-formamido-6β-(2,2,2-trichloroethoxycarbonylamino)penicillanate

Benzyl 6β-(N-2,2,2-trichloroethyoxycarbonyl-N-nonafluorobutanesulphonyl-amino)-penicillanate (100 mg; 0.13 mmol) was dissolved in dry MDC (3 ml), cooled to −5° C. and treated sequentially with bis-(trimethylsilyl)formamide (56 μl; 0.26 mmol) and triethylamine (27 μl; 0.20 mmol). After removing the cooling bath, the reaction was allowed to warm towards room temperature over 2 h. The reaction mixture was poured into ethyl aceate, washed with very dilute hydrochloric acid, brine, dried (MgSO$_4$) and evaporated. Chromatography on silica gel afforded the title product (47 mg; 68%) identical to authentic material.

EXAMPLE 28

(a) t-Butyl 7β-(Nonafluorobutanesulphonylamino)cephalosporanate t-Butyl 7-amino cephalosporanate (328 mg; 1.0 mmol) was dissolved in dry MDC (5 ml), cooled to −60° C. under argon and triethylamine (109 mg; 1.1 mmol) added, followed by nonafluorobutanesulphonic acid anhydride (624 mg; 1.1 mmol). The reaction was allowed to warm towards 0° C. over 1 h, poured into ethyl acetate, washed with dilute hydrochloric acid, saturated sodium hydrogencarbonate, brine, dried (MgSO$_4$) and evaporated. The residue was chromatographed on silica gel to afford the title product (351 mg; 58%) $\nu_{max}$ (Nujol) 1815, 1738, 1695, 1645, 1350, 1145 cm$^{-1}$; δppm (CDCl$_3$) 1.53 (9H,s), 2.09 (3H,s), 3.44 and 3.59 (2H, ABq, J 18.5 Hz), 4.82 and 5.16 L (2H, ABq, 13.5 Hz), 4.97 (1H, d, J 4.9 Hz), 5.41 (1H, d, J 4.9 Hz).

(b) t-Butyl 7β-[N-2,2,2-trichloroethoxycarbonyl-N-nonafluorobutanesulphonylamino]cephalosporanate t-Butyl 7β-(nonafluorobutanesulphonylamino)cephalosporanate (200 mg; 0.33 mmol) was dissolved in dry MDC (5 ml), cooled to −10° C. and trichloroethylchloroformate (140 mg; 0.66 mmol) added, followed by pyridine (35 mg; 0.36 mmol). The reacton mixture was poured into ethyl acetate-dilute hydrochloric acid. The organic phase was separated, washed with brine, saturated sodium hydrogencarbonate, brine, dried (MgSO$_4$) and evaporated. Chromatography on silica gel gave the title compound (222 mg; 86%). $\nu_{max}$ (Nujol) 1790, 1745, 1710, 1615 cm$^{-1}$; δppm (CDCl$_3$) 1.55 (9H, s), 2.09 (3H, s), 3.47 (2H,AA′), 4.85 and 5.12 (2H, ABq, J 13.5 Hz), 4.85 and 4.97 (2H, ABq, J 11.7 Hz), 5.06 (1H, d, J 4.82), 5.65 (1H, d, J 4.8 Hz).

(c) t-Butyl 7α-Formamido-7β-[N,2,2,2-trichloroethoxycarbonylamino-]cephalosporanate t-Butyl 7β-[N-2,2,2-trichloroethoxycarbonyl-N-nonafluorobutanesulphonylamino]-cephalosporanate (100 mg; 0.127 mmol) was dissolved in dry MDC (2 ml), cooled to −10° C. and bis-tri(methylsilyl)formamide (26 mg; 0.5 mmol) added, followed by triethylamine (14 mg; 0.139 mmol). The cooling bath was removed and the reaction warmed to room temperature over 1.75 h. The reaction was poured into ethyl acetate, washed with dilute hydrochloric acid, brine, dried (MgSO$_4$) and evaporated. Chromatography on silica gel afforded the title product (47 mg; 68%) containing 20% t-butyl 3-acetoxymethyl-7α-formamido-7β-(N-2,2,2-trichloroethoxycarbonylamino)-ceph-2-em-4-carboxylate.

EXAMPLE 29

(a) t-Butyl 7β-(N-4-nitrophenylsulphonylamino)cephalosporanate t-Butyl 7-aminocephalosporanate (1.48 g) was treated with 4-nitrophenylsulphonyl chloride using the procedure described in Example 18(A). The title compound (1.6 g) was a crystalline solid m.p. 217°–219° C.(dec). $\nu_{max}$ (Nujol) 1795, 1740, 1700, 1630, 1514, 1470, 1350, 1160 cm$^{-1}$; δ(1:1, CDCl$_3$:(CD$_3$)$_2$SO) 1.45 (9H, s), 1.99 (3H, s), 3.26 and 3.53 (2H, ABq, J 18 Hz), 4.67 and 4.96 (2H, ABq, J 14 Hz), 4.93 (1H, d, J 5 Hz), 5.33 (1H, dd, J 5 Hz and 10 Hz), 8.13 and 8.37 (4H, ABq, J 9 Hz).

(b) t-Butyl 7β-(N-2,2,2-trichloroethyloxycarbonyl-N-4-nitrophenylsulphonylamino)cephalosporanate t-Butyl 7β-(N-4-nitrophenylsulphonylamino)cephalosporanate (513 mg) was converted into the title compound (640 mg) as described in Example 18(b). m.p. 136°–137° C., $\nu_{max}$ (CHCl$_3$) 1790, 1742 (broad), 1535, 1170 cm$^{-1}$; δ(CDCl$_3$) 1.54 (9H, s), 2.05 (3H, s), 3.47 (2H, AA′), 4.72 (2H, s), 4.78 and 5.08 (2H, ABq, J 13 Hz), 5.1 (1H, d, J 5 Hz), 5.88 (1H, d, J 5 Hz) 8.34 (4H, AA′). (Found: C, 40.3; H, 3.6; N, 6.2; S, 9.1, Cl, 15.5. C$_{23}$H$_{24}$N$_3$O$_{11}$S$_2$Cl$_3$ requires C,40.1; H, 3.5; N, 6.1; S, 9.3; Cl, 15.5%).

(c) t-Butyl 7β-(2,2,2-trichloroethoxycarbonylamino)-7α-formamido-cephalosporanate t-Butyl 7-β-(N-2,2,2-trichloroethoxycarbonyl-N-4-nitrophenylsulphonylamino)cephalosporanate (138 mg) was dissolved in dry dichloromethane (3 ml) at 0° C. and bis-tri(methylsilyl)formamide (160 mg) added, followed by triethylamine (20 mg). The cooling-bath was removed. After 7 h the reaction mixture was worked up and chromatographed as described in Example 18(c) to give a product (11 mg) consisting of the title compound (40%) and t-butyl 3-acetoxymethyl-7-β-(2,2,2-trichloroethoxycarbonylamino)-7α-formamido-ceph-2-em-4-carboxylate (60%).

EXAMPLE 30

(a) Benzyl 6β-(2,4,5-trichlorophenylsulphonylamino)penicillanate

Benzyl 6-aminopenicillanate (generated from benzyl 6-aminopenicillanate, p-toluenesulphonic acid salt [2.39 g]) was converted into the title compound (1.78 g) as described in Example 18(a); $\nu_{max}$ (CHCl$_3$) 1790, 1740, 1360, 1175 cm$^{-1}$; δ(CDCl$_3$). 1.39 (3H, s), 1.58 (3H, s), 4.41 (1H, s); 5.08 (1H, dd, J 4 and 10 Hz), 5.15 (2H, s), 5.48 (1H, d, J 4 Hz), 5.93 (1H, d, J 10 Hz, exch.D$_2$O), 7.34 (5H, s), 7.63 (1H, s), 8.15 (1H, s).

(b) Benzyl 6β-(N-2,2,2-trichloroethoxycarbonyl-N-2,4,5-trichlorophenylsulphonylamino)penicillanate Benzyl 6β-(2,4,5-trichlorophenylsulphonylamino)-pencillanate (1.099 g) was converted into the title compound (1.363 g) as described in Example 18(b); $\nu_{max}$ (Nujol) 1805, 1790, 1745, 1380, 1160 cm$^{-1}$; δ(CDCl$_3$) 1.43 (3H, s), 1.67 (3H, s), 4.55 (1H, s), 4.62 and 4.81 (2H, ABq, J 12 Hz), 5.19 (2H, s), 5.58 (1H, d, J 4 Hz), 5.92 (1H, d, J 4 Hz) 7.35 (5H,s), 7.63 (1H, s), 8.32 (1H, s).

(c) Benzyl 6α-formamido-6β-(2,2,2-trichloroethoxycarbonylamino)penicillanate Benzyl 6β-(N-2,2,2-trichloroethoxycarbonyl-N-2,4,5-trichlorophenylsulphonylamino)penicillanate (182 mg) was treated with bis-(trimethylsilyl)formamide (190 mg) and triethylamine (38 mg). After 7½ h at room temperature the solution was worked up as in Example 18(c). Chromatographed on silica gel afforded the title compound (21 mg), identical to authentic material.

EXAMPLE 31

(a) Benzyl 6β-(p-toluenesulphonylamino)penicillate

Benzyl 6-aminopenicillanate, p-toluenesulphonic acid salt (2.39 g) was suspended in dichloromethane (25 ml) at −20° C. and triethylamine (1.11 g) added, followed by p-toluenesulphonyl chloride (1.05 g). The solution was allowed to warm to room temperature. After 70 h the reaction mixture was poured into ethyl acetate and the solution washed successively with dilute hydrochloric acid, brine, aqueous sodium hydrogen carbonate, brine, dried and evaporated. Chromatography on silica gel gave the title compound (1.25 g; $\nu_{max}$ (CDCl$_3$), 1790, 1740, 1350, 1160 cm$^{-1}$; δ(CDCl$_3$) 1.32 (3H, s), 1.52 (3H, s), 2.39 (3H, s), 4.38 (1H, s), 5.02 (1H, dd, J 4 and 11 Hz), 5.29 (1H, d, J 4 Hz), 5.48 L (1H, d J 11 Hz), 7.25 (2H, d, J 8 Hz) 73, (5H, s) 7.72 (2H, d, J 8 Hz).

(b) Benzyl 6β-(N-2,2,2-trichloroethoxycarbonyl-N-p-toluenesulphonylamino)penicillanate Benzyl 6β-(p-toluenesulphonylamino)penicillanate (920 mg) was converted into the title compound (1.0 g) as described in Example 18(b); $\nu_{max}$ (CDCl$_3$) 1790, 1745, 1380, 1160 cm$^{-1}$; δ(CDCl$_3$), 1.31 (3H, s), 1.64 (3H, s,), 2.42 (3H, s), 4.52 (1H, s), 4.62 and 4.78 (2H, ABq, J 12 Hz) 5.16 (2H, s), 5.55 (1H, d, J 4 Hz), 5.66 (1H, d, J 4 Hz), 7.25 (2H, d, J 8 Hz), 7.89 (2H, d, J 8 Hz).

(c) Benzyl 6β-(N-2,2,2-trichloroethoxycarbonyl-N-p-toluenesulphonylamino)penicillanate-1-α-oxide Benzyl 6β-(N-2,2,2-trichloroethoxycarbonyl-N-p-toluenesulphonylamino)penicillanate (318 mg) was dissolved in dichloromethane (5 ml) at −10° C. and peracetic acid (0.8 ml of 2.54% W/V solution in acetic acid) added. The temperature was raised to +10° and after 3 h the solution was evaporated to dryness. Toluene was added and the process was repeated (×3). The residue was chromatographed on silica gel to give the title compound (221 mg); $\nu_{max}$ (CHCl$_3$) 1805, 1745(broad), 1385, 1170, 1060(broad) cm$^{-1}$; δ(CDCl$_3$), 1.28 (3H, s), 1.65 (3H, s), 2.40 (3H, s) 4.44 (1H, s), 4.68 (2H, s), 4.77 (1H, d, J 4 Hz) 5.22 (2H, AA'), 6.00 (1H, d, J 4 Hz) 7.3 (2H, d, J 8.5 Hz). 7.88 (2H, d, J 8.5 Hz).

(d) Benzyl 6β-(2,2,2-trichloroethoxycarbonylamino)-6α-formamidopenicillanate-1-α-oxide Benzyl 6β-(N-2,2,2-trichloroethoxycarbonylamino-N-p-toluenesulphonylamino)penicillanate-1-α-oxide (65 mg) was dissolved in dichloromethane (3 ml) and bis-(trimethylsilyl)formamide (76 mg) was added, followed by triethylamine (10 mg). After 20 min the solution was worked up as in Example 18(c). Chromatography on silica gel gave the title compound (22 mg) identical to an authentic sample.

EXAMPLE 31

Benzyl 6α-formamido-6β-[D-2-(4-nitrobenzyloxycarbonylamino)-2-phenylacetamido]penicillanate Silver acetate (0.867 g, 5.2 mmol) was added in one portion to a solution of benzyl 6α-methylthio-6β-[D-2-(4-nitrobenzyloxycarbonylamino)-2-phenylacetamido]penicillanate (3.46 g, 5.2 mmol) and N,N-bis(trimethylsilyl)formamide (1.98 g, 10.4 mmol) in N,N-dimethylformamide (40 ml), and the reaction mixture was stirred at room temperature for 0.5 h. It was then diluted with ethyl acetate (∼100 ml), filtered through a pad of Celite, and the filtrate was washed with water (5×30 ml). After washing with brine (30 ml), the organic solution was dried over magnesium sulphate and then evaporated to dryness to afford the crude product. This was chromatographed on silica gel 60 (<230 mesh ASTM) eluting with hexane/ethyl acetate 1:1 grading to 1:2, to afford the title compound (1.79 g, 52%); $\nu_{max}$ (CH$_2$Cl$_2$) 1785, 1740, 1690, 1605 cm$^{-1}$; δ(CDCl$_3$) 0.93 and 1.17 (6H, 2s, 2—CH$_3$s), 4.41 (1H, s, 3—H), 5.16 L (4H, s, ArCH$_2$), 5.64 (2H, m, —CHNHCO and 5—H), 6.89 (1H, s, NH), 7.39 (12H, m, aromatic protons), 8.14 (3H, m, aromatic protons and CHO) and 8.85 (1H, m, NH).

I claim:

1. A process for the preparation of a compound of formula (III) or a salt thereof:

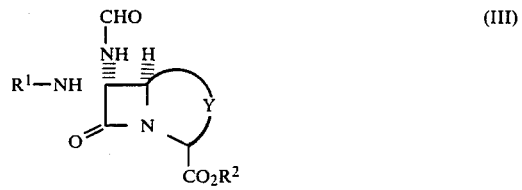

wherein R$^1$ is an acyl group, R$^2$ is hydrogen or a readily removable carboxyl protecting group; and Y is

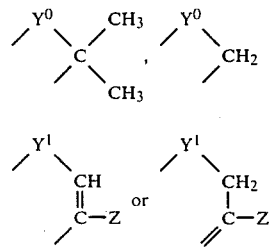

wherein Y$^o$ is sulphur, SO or SO$_2$, Y$^1$ is oxygen, sulphur, SO, SO$_2$ or —CH$_2$— and Z represents hydrogen, halogen, or an organic group such as C$_{1-4}$ alkoxy, —CH$_2$Q or —CH=CH—Q
wherein Q represents hydrogen, halogen, hydroxy, mercapto, cyano, carboxy, carbamoyloxy, carboxylic ester, C$_{1-4}$ alkyloxy, acyloxy, aryl, heterocyclyl group bonded via carbon, a heterocyclylthio group or a nitrogen containing heterocyclic group bonded via nitrogen, which process comprises treating an intermediate imine of formula (IV):

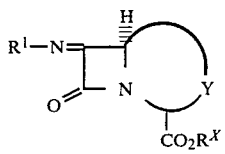

(IV)

wherein any reactive groups may be protected; $R^1$ and Y are as hereinbefore defined; and $R^x$ is a readily removable carboxy protecting group; with a nucleophilic derivative of formamide and thereafter, if necessary, carrying out one or more of the following steps:
(i) removing any protecting groups;
(ii) converting a group $R^x$ to a group $R^2$;
(iii) converting one group Z into a different group Z;
(iv) converting the product into a salt.

2. A process as claimed in claim 1 wherein the nucleophilic derivative of formamide is an N,N-bis(tri-loweralkylsilyl)formamide.

3. A process according to claim 1 wherein the nucleophilic derivative of formamide is N,N-bis-trimethylsilylformamide.

4. A process as claimed in claim 1 wherein Y is

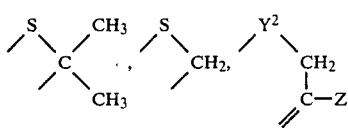

wherein $Y^2$ is oxygen, sulphur or —CH$_2$—.

5. A process as claimed in claim 1 wherein Y is —S—C(CH$_3$)$_2$—.

6. A process as claimed in claim 1 for the preparation of a compound of formula (V) or a pharmaceutically acceptable salt or in vivo hydrolysable ester thereof:

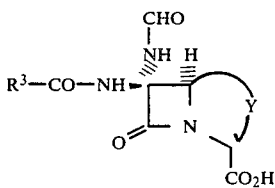

(V)

wherein $R^3$ is a group such that $R^3$—CO—NH— is an acylamino group.

7. A process as claimed in claim 1 for the preparation of a compound of formula (VI) or a pharmaceutically acceptable salt or in vivo hydrolysable ester thereof:

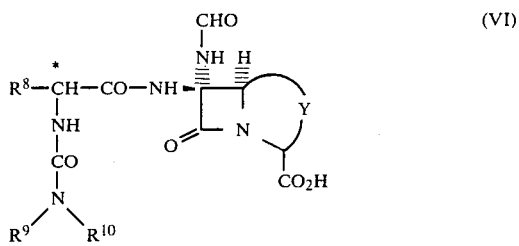

(VI)

wherein $R^8$ is phenyl, substituted phenyl, cyclohexenyl, cyclohexadienyl, or a 5- or 6-membered heterocyclic ring containing up to three hetero-atoms selected from oxygen, sulphur or nitrogen, optionally substituted with hydroxy, amino, halogen, substituted amino or $C_{1-6}$ alkoxy; $R^9$ is hydrogen or a $C_{1-6}$ alkyl group and $R^{10}$ is an optionally substituted 5- or 6-membered heterocyclic group containing one or two nitrogen heteroatoms; or $R^9$ and $R^{10}$ together with the nitrogen atom to which they are attached form an optionally substituted five or six-membered heterocyclic group containing one or two nitrogen heteroatoms.

8. A process as claimed in claim 1 for the preparation of a compound of formula (VIII) or a pharmaceutically acceptable salt or in vivo hydrolysable ester thereof:

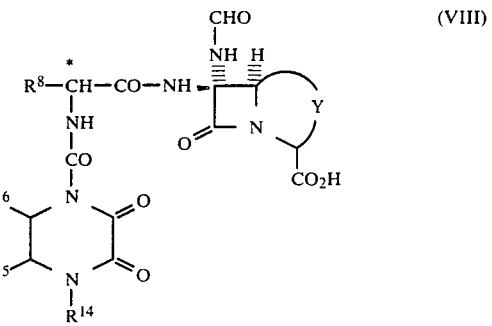

(VIII)

wherein $R^{14}$ represents hydrogen, $C_{1-6}$ alkyl, substituted alkyl, aryl, or aralkyl; $R^{15}$ and $R^{16}$ are the same or different and represent hydrogen, $C_{1-6}$ alkyl, substituted alkyl, halogen, amino, hydroxy or $C_{1-6}$ alkoxy or $R^{15}$ and $R^{16}$ form the residue of 5- or 6-membered carbocyclic or heterocyclic ring.

9. A process is claimed in claim 1 for the preparation of sodium 6β-[D-2-[(4-ethyl-2,3-dioxopiperazin-1-yl)carbonylamino]-2-(3,4-dihydroxyphenyl)acetamido]-6α-formamidopenicillanate.

* * * * *